United States Patent
Böck et al.

(10) Patent No.: US 9,687,617 B2
(45) Date of Patent: *Jun. 27, 2017

(54) NEBULIZER

(71) Applicant: Boehringer Ingelheim International GmbH, Ingelheim am Rhein (DE)

(72) Inventors: Georg Böck, Laupheim (DE); Florian Witte, Schwabenheim (DE); Ralf Thömmes, Willich (DE); Christian Golberg, Gelsenkirchen (DE); Timo von Brunn, Dortmund (DE); Andreas Fiol, Norderstedt (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 577 days.

This patent is subject to a terminal disclaimer.

(21) Appl. No.: 14/095,147

(22) Filed: Dec. 3, 2013

(65) Prior Publication Data

US 2014/0158118 A1 Jun. 12, 2014

Related U.S. Application Data

(62) Division of application No. 11/420,109, filed on May 24, 2006, now Pat. No. 8,656,910.

(30) Foreign Application Priority Data

May 24, 2005 (DE) .................... 10 2005 024 439

(51) Int. Cl.
*A61M 11/00* (2006.01)
*A61M 15/00* (2006.01)
(Continued)

(52) U.S. Cl.
CPC ........ *A61M 15/009* (2013.01); *A61M 11/007* (2014.02); *A61M 11/02* (2013.01);
(Continued)

(58) Field of Classification Search
CPC .. A61M 15/009; A61M 11/007; A61M 11/02; A61M 15/0065; A61M 15/0081;
(Continued)

(56) References Cited

U.S. PATENT DOCUMENTS 3,802,604 A   4/1974   Morane et al.
5,135,137 A   8/1992   Rudick
(Continued)

FOREIGN PATENT DOCUMENTS

DE   27 54 100 A1   6/1978
EP   1 003 478 B1   5/2000
(Continued)

*Primary Examiner* — Steven Douglas
(74) *Attorney, Agent, or Firm* — David S. Safran

(57) ABSTRACT

A nebulizer for a fluid, particularly for medical aerosol treatment is proposed. To allow easier operation and confer improved operational reliability a sealed container holding the fluid is already arranged in the nebulizer when it is supplied and the nebulizer is constructed so that the container is opened inside the nebulizer before or during the first use of the nebulizer. For this purpose, a transportation lock is provided for the sealed container which, in the delivery state, is in engagement with the sealed container in a manner preventing the sealed container from moving axially in the nebulizer.

20 Claims, 39 Drawing Sheets

(51) Int. Cl.
*B05B 11/00* (2006.01)
*A61M 11/02* (2006.01)

(52) U.S. Cl.
CPC ..... *A61M 15/0065* (2013.01); *B05B 11/0008* (2013.01); *B05B 11/0054* (2013.01); *A61M 15/0026* (2014.02); *A61M 15/0073* (2014.02); *A61M 15/0081* (2014.02); *A61M 2205/276* (2013.01); *B05B 11/3091* (2013.01)

(58) Field of Classification Search
CPC .......... A61M 15/0073; A61M 15/0026; A61M 2205/276; B05B 11/0054; B05B 11/0008; B05B 11/3091
USPC .......... 128/200.14, 200.21; 222/82, 105, 136
See application file for complete search history.

(56) References Cited

U.S. PATENT DOCUMENTS

| | | | |
|---|---|---|---|
| 5,497,944 | A | 3/1996 | Weston et al. |
| 5,503,302 | A | 4/1996 | DeJonge |
| 5,509,578 | A | 4/1996 | Livingstone |
| 5,547,131 | A | 8/1996 | Brace |
| 5,584,417 | A | 12/1996 | Graf et al. |
| 5,662,271 | A | 9/1997 | Weston et al. |
| 5,833,088 | A | 11/1998 | Kladders et al. |
| 6,223,933 | B1 | 5/2001 | Hochrainer et al. |
| 6,412,659 | B1 | 7/2002 | Kneer |
| 6,464,105 | B1 | 10/2002 | Rolle et al. |
| 6,626,328 | B2 | 9/2003 | Ritsche et al. |
| 6,626,379 | B1 | 9/2003 | Ritsche et al. |
| 6,708,846 | B1 * | 3/2004 | Fuchs .................... A61M 11/06 222/327 |
| 6,726,124 | B2 | 4/2004 | Jaeger et al. |
| 6,918,547 | B2 | 7/2005 | Jaeger et al. |
| 8,656,910 | B2 * | 2/2014 | Boeck ............... A61M 15/0065 128/200.14 |
| 2003/0064032 | A1 | 4/2003 | Lamche et al. |

FOREIGN PATENT DOCUMENTS

| | | |
|---|---|---|
| WO | 91/14468 A1 | 10/1991 |
| WO | 96/06011 A2 | 2/1996 |
| WO | 97/12687 A1 | 4/1997 |

* cited by examiner

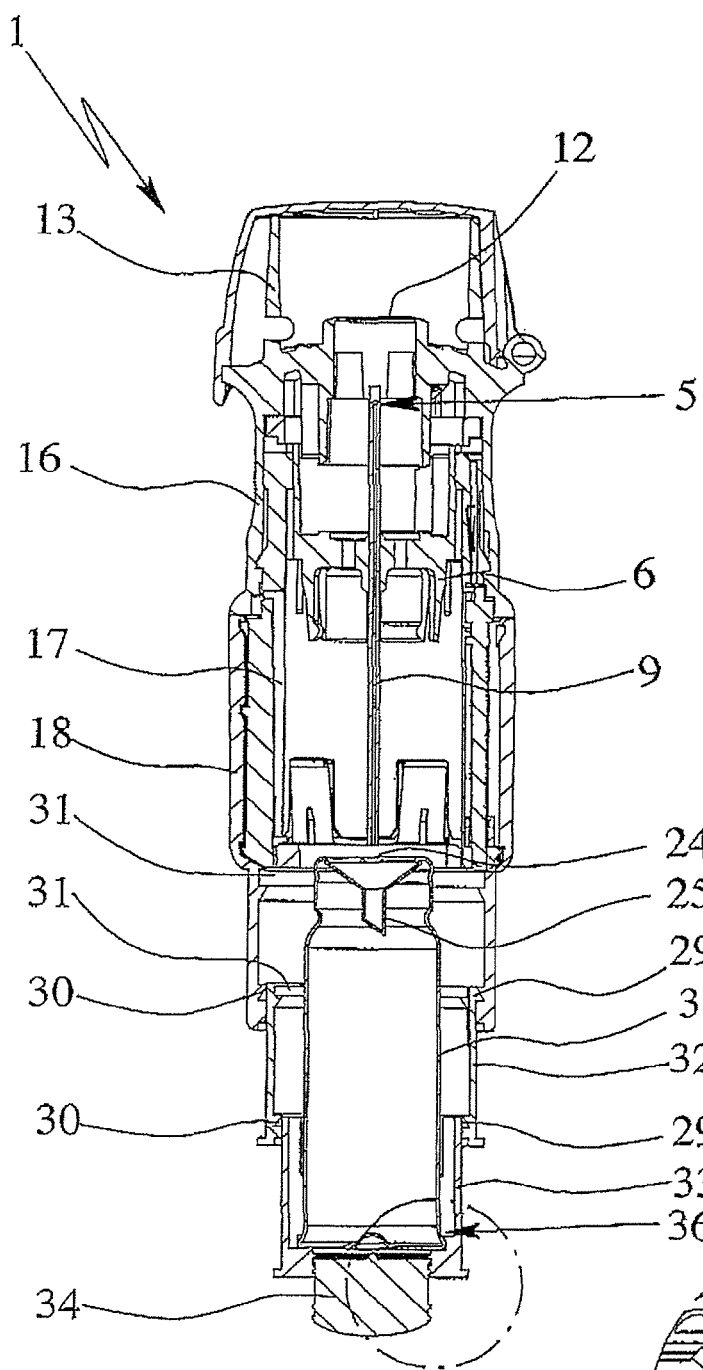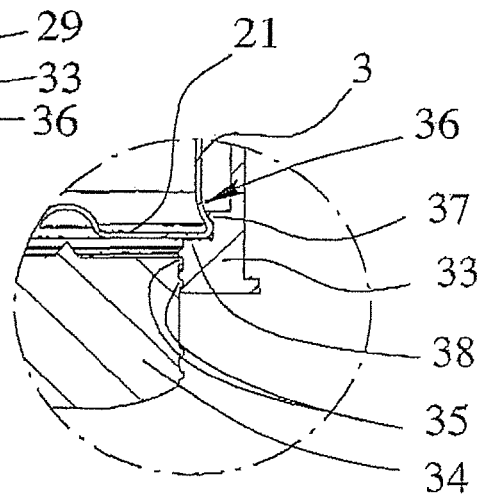
Fig. 5
Fig. 6

őm# NEBULIZER

CROSS REFERENCE TO RELATED APPLICATION

This application is a division of commonly owned, co-pending U.S. patent application Ser. No. 11/420,109, filed May 24, 2006.

BACKGROUND OF THE INVENTION

Field of the Invention

The present invention relates to a nebulizer for a fluid having a preferably insertable container containing the fluid, which is closed off, in particular sealed, in the delivered state.

Description of Related Art

The starting point for the present invention is a nebulizer in the form of an inhaler sold under the trademark RESPIMAT®, which is illustrated in its basic structure in International Patent Application Publication WO 91/14468 A1 (corresponding U.S. Pat. Nos. 5,497,944 and 5,662,271) and in a specific embodiment in FIGS. 6a, 6b of International Patent Application Publication WO 97/12687 A1 (corresponding U.S. Pat. Nos. 6,726,124 and 6,918,547) and in FIGS. 1 and 2 of the accompanying drawings of this application. The nebulizer has, as a reservoir for fluid which is to be atomized, an insertable rigid container with an inner bag containing the fluid and a pressure generator with a drive spring for delivering and atomizing the fluid.

To supplement the disclosure of the present application reference is made to the complete disclosure of both WO 91/14468 A1 and WO 97/12687 A1 and their U.S. Patent counterparts indicated above. Generally, the disclosure contained therein preferably relates to a nebulizer with a spring pressure of 5 to 200 MPa, preferably 10 to 100 MPa on the fluid, with a volume of fluid delivered per stroke of 10 to 50 µl, preferably 10 to 20 µl, most preferably about 15 µl. The fluid is converted into an aerosol, the droplets of which have an aerodynamic diameter of up to 20 µm, preferably 3 to 10 µm. Furthermore, the disclosure contained therein preferably relates to a nebulizer of cylindrical shape of about 9 cm to about 15 cm and about 2 cm to about 5 cm wide and with a jet spray angle of 20° to 160°, preferably 80° to 100°. These values also apply to the nebulizer according to the teaching of the present invention as particularly preferred values.

Before being used for the first time, the nebulizer is opened by undoing a lower housing part and the sealed container is inserted in the nebulizer. The container is opened by a delivery tube which is inserted into the inner bag as the container is put in. Then, the lower housing part is pushed on again.

By rotating the lower housing part of the nebulizer, the drive spring can be put under tension and fluid can be sucked into a compression chamber of the pressure generator. As it is tensioned, the container is moved into the lower housing part in a single movement within the nebulizer, and when tensioned for the first time, it is pierced through its base by a piercing element in the lower housing part to allow air in or out. After manual operation of a locking element, the fluid in the pressure chamber is put under pressure by the drive spring and is delivered through a nozzle into a mouthpiece as an aerosol, without the use of propellant gas.

After opening the nebulizer, the empty container can be replaced by a full one and the nebulizer can then be used again.

SUMMARY OF THE INVENTION

A primary object of the present is to provide a nebulizer which is easier to operate and has improved operational reliability.

The object is achieved by a nebulizer as described below.

A basic idea of the present invention is that, even in its delivered state, the nebulizer has a sealed container provided therein and the nebulizer is constructed so that the container is opened inside the nebulizer before or during the first use of the nebulizer. This basic idea is hereinafter referred to as a "pre-installed container" for short. This makes operation easier as there is no need to open the nebulizer, insert the container and close the nebulizer. Moreover, undesirable soiling or damage to the nebulizer caused by incorrect handling when inserting the container can thus be ruled out. Accordingly, there is better operational safety as it is impossible for the container to be wrongly inserted or otherwise misused during insertion.

Another aspect of the present invention which can also be implemented independently involves constructing the nebulizer so that the container is not replaceable and in particular cannot be removed. This rules out replacement of the container. This again leads to easier operation and hence improved operational reliability. This also prevents the nebulizer from being used or re-used in an undesirable or unauthorized manner.

In particular, the nebulizer cannot be opened and the lower housing part cannot be removed in order to replace the empty container with a full one in an undesirable manner.

The combination of the pre-installed container and the construction which makes the container non-replaceable results in particularly easy operation and high operational reliability as the user can only use the nebulizer as a single-use item until the container is empty, and undesirable or unauthorized further use of the nebulizer is prevented by the fact that the container cannot be replaced.

However, correspondingly, easy operation and improved operational reliability for the user can also be achieved if the container is pre-installed at the pharmacy, for example, i.e., by trained staff, and optionally, opened at the same time provided that the container is made non-exchangeable, in particular, the nebulizer cannot be opened by the user.

Further advantages, features, characteristics and aspects of the present invention will become apparent from the following description of some preferred embodiments with reference to the accompanying drawings:

BRIEF DESCRIPTION OF THE DRAWINGS

FIG. 5 is a schematic section through a proposed nebulizer according to a second embodiment in the delivered state with a sealed container incorporated therein;

FIG. 6 shows the broken line encircled detail of FIG. 5 in an enlarged view;

FIG. 12 is a diagrammatic perspective view of a proposed nebulizer according to a fourth embodiment having an actuating member similar to the third embodiment, but not pushed on;

FIG. 38 is a perspective side side view, partly in section, of the housing part of the nebulizer according to FIG. 34 with the inner part partially pushed in;

FIG. 39 is a perspective side side view, partly in section, of the housing part of the nebulizer according to FIG. 34, with the inner part totally pushed in;

DETAILED DESCRIPTION OF THE INVENTION

Figure 1:
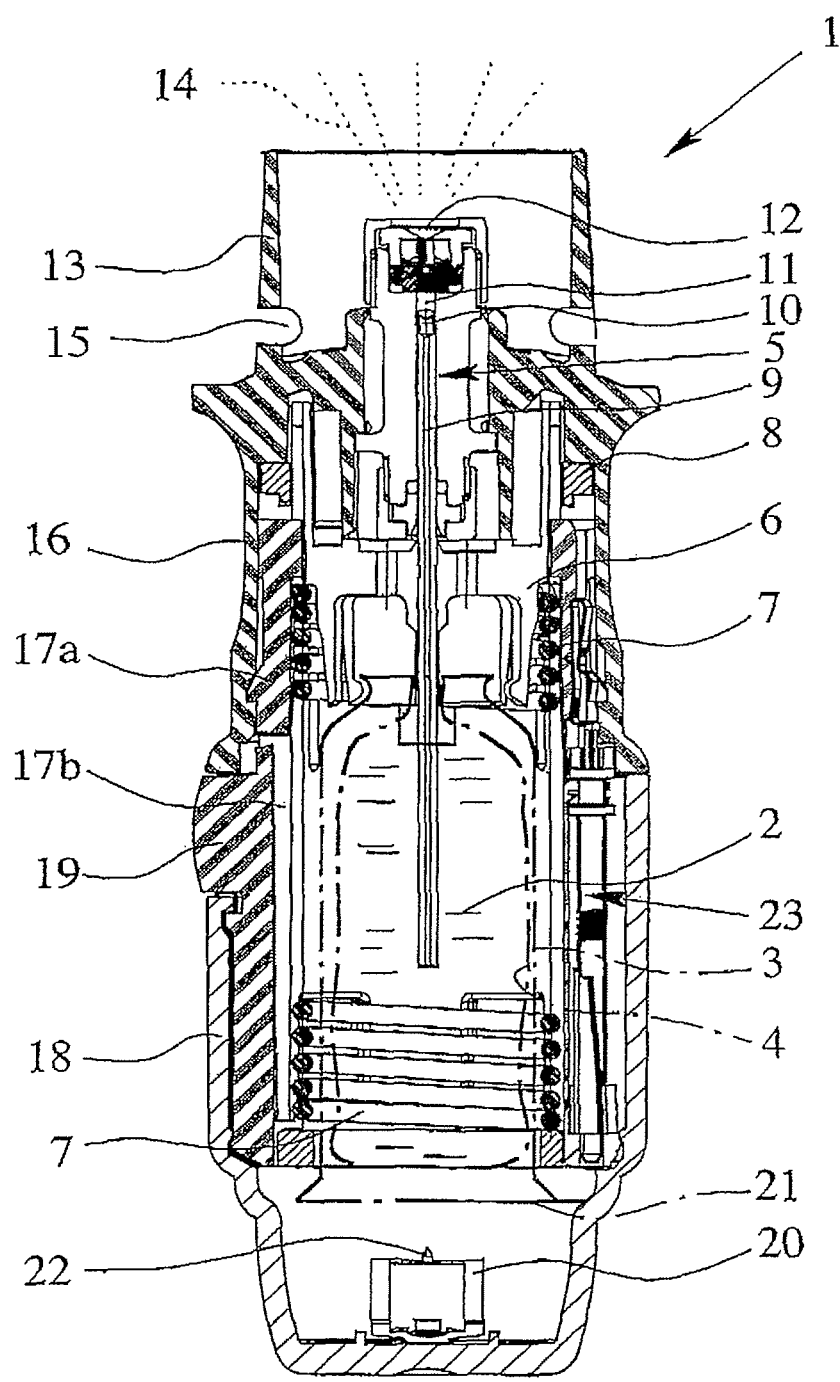
FIG. 1 shows a non-schematic section through a known nebulizer in the untensioned state.

In the Figures, the same reference numerals have been used for identical or similar parts, resulting in corresponding or comparable properties and advantages, even if the associated description is not repeated.

FIGS. 1 & 2 show a known nebulizer 1 for atomizing a fluid 2, particularly a highly effective pharmaceutical composition or the like, diagrammatically shown in the untensioned state (FIG. 1) and in the tensioned state (FIG. 2). The nebulizer 1 is constructed in particular as a portable inhaler and preferably operates without propellant gas.

When the fluid 2, preferably a liquid, more particularly a pharmaceutical composition, is nebulized, an aerosol is formed, which can be breathed in or inhaled by a user (not shown). Usually, the inhaling is performed at least once a day, more particularly several times a day, preferably at set intervals, depending on the complain from which the patient is suffering.

The known nebulizer 1 has an insertable and preferably exchangeable container 3 containing the fluid 2. The container thus forms a reservoir for the fluid 2 which is to be nebulized. Preferably, the container 3 contains an amount of fluid 2 or active substance which is sufficient to provide up to 200 dosage units, for example, i.e. to allow up to 200 sprays or applications. A typical container 3, as disclosed in International Patent Application Publication WO 96/06011 A1 and corresponding U.S. Pat. No. 5,833,088, holds a volume of about 2 to 10 ml.

The container 3 is substantially cylindrical or cartridge-shaped and once the nebulizer 1 has been opened the container can be inserted therein from below and changed if desired. It is preferably of rigid construction, the fluid 2, in particular, being held in a collapsible bag 4 in the container 3.

The nebulizer 1 also has a pressure generator 5 for conveying and nebulizing the fluid 2, particularly in a preset and optionally adjustable dosage amount. The pressure generator 5 has a holder 6 for the container 3, an associated drive spring 7, only partly shown, with a locking element 8 which can be manually operated to release it, a conveying tube 9 with a non-return valve 10, a pressure chamber 11 and an expulsion nozzle 12 in the region of a mouthpiece 13. The container 3 is fixed in the nebulizer 1 via the holder 6 such that the conveying tube 9 penetrates into the container 3. The holder 6 may be constructed so that the container 3 is able to be exchanged.

As the drive spring 7 is axially tensioned, the holder 6 with the container 3 and the conveying tube 9 is moved downwards in the drawings and fluid 2 is sucked out of the container 3 into the pressure chamber 11 of the pressure generator 5 through the non-return valve 10.

During the subsequent relaxation after actuation of the locking element 8, the fluid 2 in the pressure chamber 11 is put under pressure as the conveying tube 9 with its now closed non-return valve 10 is moved back upwards by the relaxation of the drive spring 7 and now acts as a pressing ram. This pressure forces the fluid 2 through the expulsion nozzle 12, whereupon it is nebulized into an aerosol 14, as shown in FIG. 1. The droplet size of the particles for a device of the RESPIMAT® type has already been discussed hereinbefore.

A user (not shown) can inhale the aerosol 14, while an air supply can be sucked into the mouthpiece 13 through at least one air supply opening 15.

The nebulizer 1 comprises an upper housing part 16 and an inner part 17 which is rotatable relative thereto (FIG. 2) having an upper part 17a and a lower part 17b (FIG. 1), while an, in particular, manually operable housing part 18 is releasably fixed, particularly fitted onto the inner part 17, preferably by means of a retaining element 19. In order to insert and/or replace the container 3, the housing part 18 can be detached from the nebulizer 1.

Figure 2:
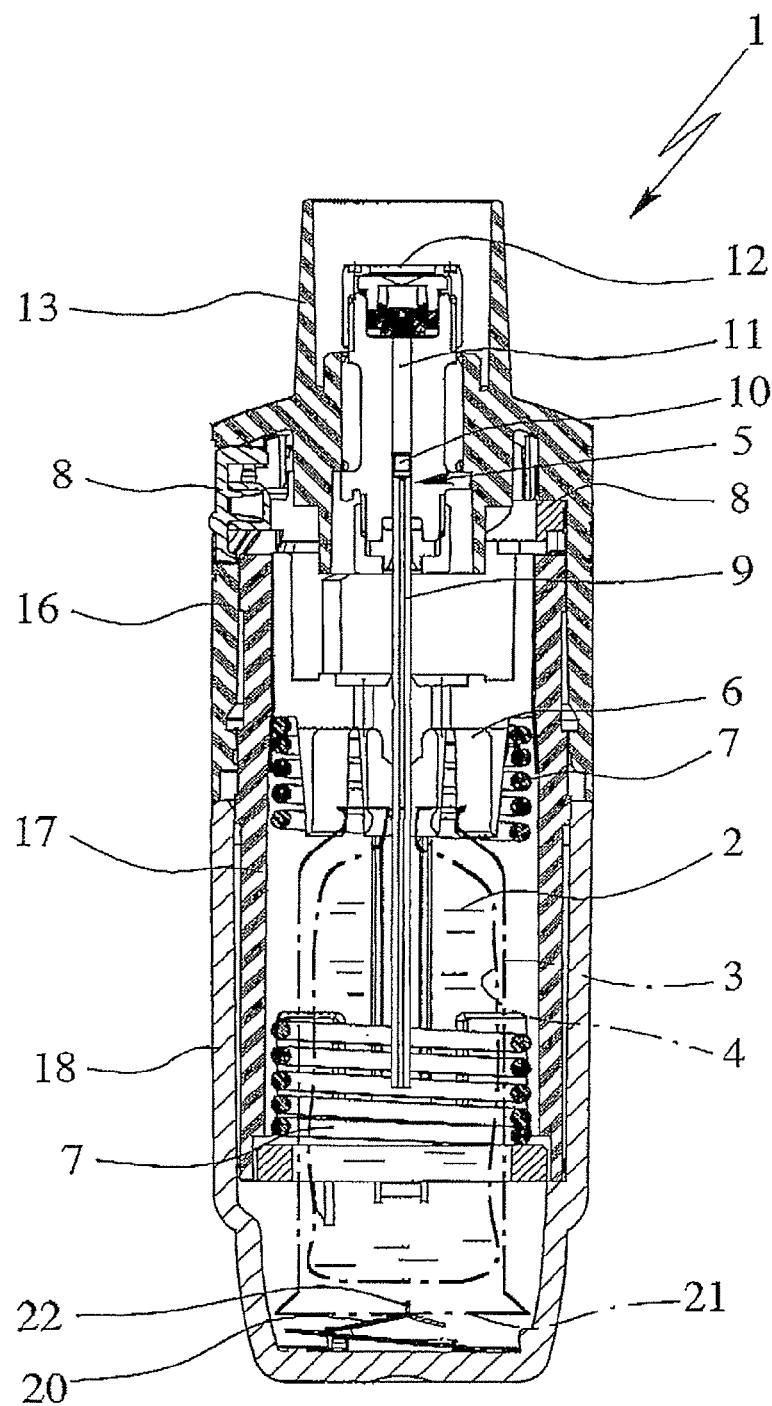
FIG. 2 shows a schematic section, rotated through 90° compared with FIG. 1, through the known nebulizer in the tensioned state.

The housing part 18 can be rotated relative to the upper housing part 16, carrying with it the part 17b of the inner part 17 which is lower down in the drawings. As a result, the drive spring 7 is tensioned in the axial direction by means of a gear (not shown) acting on the holder 6. During tensioning, the container 3 is moved axially downwards until the container 3 assumes an end position as shown in FIG. 2. In this state, the drive spring 7 is under tension. During the nebulizing process, the container 3 is moved back into its original position by the drive spring 7. Thus, the container 3 executes a lifting movement during the tensioning process and during the atomizing process.

The housing part 18 preferably forms a cap-like lower housing part and fits around or over a lower free end portion of the container 3. As the drive spring 7 is tensioned, the container 3 moves with its end portion (further) into the housing part 18 or towards the end face thereof, while an axially acting spring 20 arranged in the housing part 18 comes to bear on the base 21 of the container and pierces the container 3 or a base seal thereon with a piercing element 22 when the container makes contact with it for the first time, to allow air in.

The nebulizer 1 comprises a monitoring device 23 which counts the actuations of the nebulizer 1, preferably by detecting the rotation of the inner part 17 relative to the upper part 16 of the housing.

The construction and mode of operation of twelve embodiments of a proposed nebulizer 1 will now be described in more detail, referring to FIGS. 3 to 42, but emphasizing only the essential differences from the nebulizer 1 according to FIGS. 1 & 2. The remarks relating to FIGS. 1 & 2 thus apply accordingly or in a supplementary capacity, while any desired combinations of features of the nebulizer 1 according to FIGS. 1 & 2 and the nebulizer 1 according to the embodiments described below or with one another are possible, except to the extent inconsistent with the improvements described below.

Figure 3:
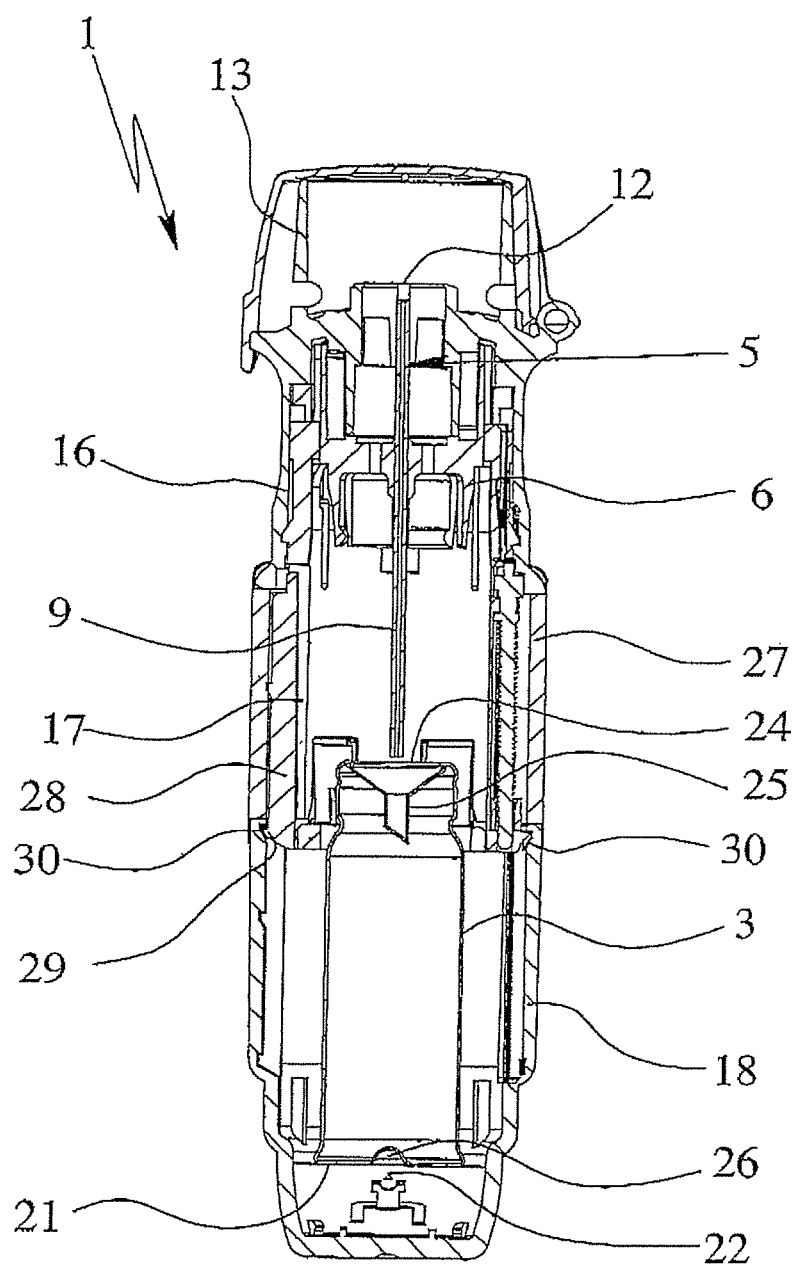
FIG. 3 is a schematic section through a proposed nebulizer according to a first embodiment in the delivered state with a sealed container incorporated therein.
Figure 4:
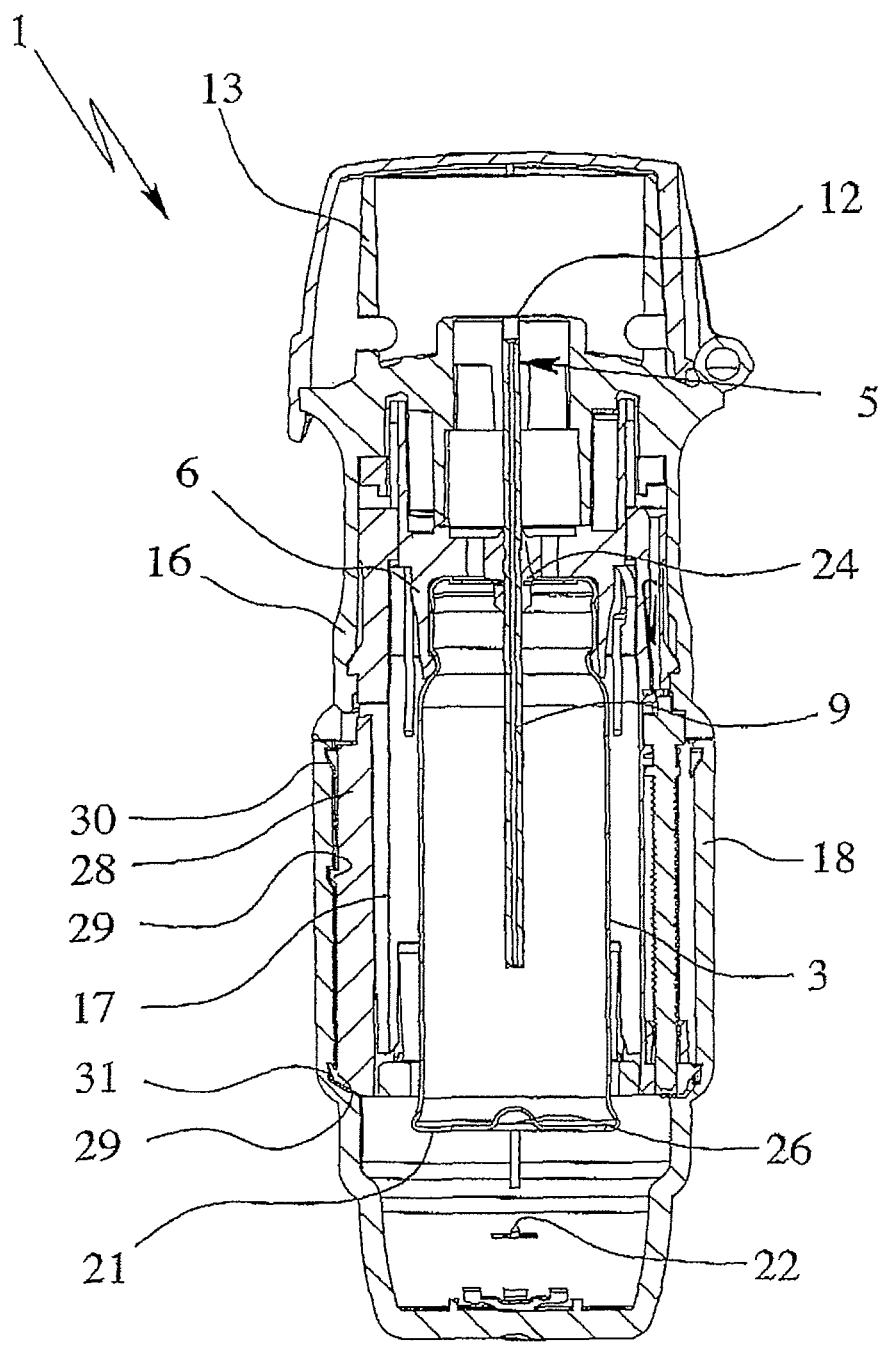
FIG. 4 is a schematic section through the nebulizer according to FIG. 3 in the activated state or with the container open.

FIGS. 3 & 4 show, in a diagrammatic sectional views, a first embodiment of the proposed nebulizer 1. FIG. 3 shows the delivered state with the container 3 sealed. FIG. 4 shows the activated state, i.e., after the container 3 has been opened.

As proposed, the (still) closed container 3 is already mounted in the nebulizer 1 in its delivered state, as shown in FIG. 3. In the closed state, in the embodiments shown, an outer seal 24 on the head end of the container 3 and a septum 25, a membrane, a plastic seal or the like provided inside the container 3 (only partly shown in the drawings) have not yet been opened. Moreover, in the closed state, in the embodiments shown, a vent opening 26 in the base of the container 3, which can be opened by means of the piercing element 22, is sealed, i.e., not yet pierced. It is noted that the container 3 may also have fewer and/or different opening possibilities depending on the particular construction.

In all the proposed embodiments, the nebulizer 1 is constructed so that the container 3 is or can be opened inside the nebulizer 1 before or during the first use of the nebulizer 1. The container 3 has already been opened, in particular, when the seal 24 and the septum 25 or the like have been opened. This is also referred to hereinafter as the activated state, for short. The piercing or opening of the vent opening 26 may be carried out separately, particularly later on when the nebulizer 1 is tensioned (for the first time).

It is proposed that the opening of the container 3 is carried out, in particular, by means of a delivery element, particularly conveying tube 9 or the like, preferably by piercing the container 3 or insertion into the container 3. By a suitable relative movement, particularly in the longitudinal direction or direction of lifting of the container 3 relative to the conveying tube 9, the conveying tube 9 pierces the seal 24 and is inserted through the septum 25 into the interior of the container 3, particularly into the bag 4, whereby the container 3 is opened, i.e., a fluid connection is formed for the fluid 2 to escape from the container 3. The container 3 is thus opened at the head end, in particular.

During the normal tensioning and atomizing strokes the container 3 is then preferably moved together with the conveying element or conveying tube 9 by means of the holder 6, whereby the fluid connection produced is maintained and the container 3 is preferably thus constantly open.

The ventilation provided, preferably at the base, as mentioned above by opening the vent opening 26 may be carried out before, during or after the above mentioned opening of the container 3, particularly at the head end, depending on the particular embodiment or requirements.

In the first embodiment, the container 3 is preinstalled and the housing part 18 in the delivered state has not been fully pushed on in the axial direction. Rather, a securing member 27 is mounted between the housing part 18 and the upper housing part 16, so that the housing part or lower part 18 is pressed far enough away from the upper housing part 16 to be able to hold the (still) sealed container 3 axially away from the conveying tube 9.

In the non-activated distant position the housing part 18 is preferably secured by means of at least one latching arm 28 mounted on the upper housing part 16 or inner part 17, so that it cannot be lost and in particular cannot be released. Preferably, the latching arm 28 engages with a latching lug 29 in a latching recess 30 in the housing part 18 and thereby secures the housing part 18 against total axial removal by interlocking engagement. However, other constructional solutions are also possible.

In particular, the housing part or lower part 18 of the nebulizer 1 can no longer be detached from the nebulizer 1 after it has been (partially) axially pushed on for the first time, i.e., the nebulizer 1 cannot be opened any longer, with the result that the container 3 cannot be changed, i.e., cannot be removed again.

In the first embodiment, the securing member 27 is at least substantially hollow cylindrical and is disposed axially between the housing part 18 and the upper housing part 16. To activate the nebulizer 1, i.e., push the housing part 18 fully on in the axial direction and thereby open the container 3, the securing member 27 first has to be removed. In the first embodiment, the securing member 27 is constructed in the manner of a banderol or the like, made of plastics, for example, and can be manually opened, removed or destroyed. The securing member 27 may alternatively or simultaneously form or constitute a seal of origin. However, other embodiments of the securing member 27 are also possible, e.g., in the form of a security tag or the like.

Once the security member 27 has been removed a user can push the housing part 18 fully on in the axial direction and thereby bring about the activated state of the nebulizer 1, i.e., open the container 3 by inserting the conveying element or conveying tube 9. FIG. 4 shows this activated state with the housing part 18 pushed fully on. In this pushed on state, the housing part 18 is preferably secured or held again by interlocking engagement, particularly by the engagement of the latching arm 28 or latching lug 29 in a corresponding further latching recess 31 or by means of some other mechanical securing device.

FIG. 4 shows the nebulizer 1 or container 3 in the activated state, the container 3 is already open and the housing part 18 has been pushed fully on in the axial direction. In order to bring the holder 6 into engagement with the container 3 at the head end and then be able to move the container 3 over it for the tensioning and pressing strokes, it may be necessary to tension the nebulizer 1 for the first time. During this tensioning process, the holder 6 is moved together with the conveying tube 9 axially towards or into the housing part 18, thus bringing the holder 6 into engagement with the container 3 and preferably also pressing the container 3 against the piercing element 22 in the region of the base of the housing part 18 and thereby piercing or opening the vent opening 26. FIG. 4 shows the nebulizer 1 in the relaxed state, i.e., after the first atomization, in particular. The holder 6 is engaged with the container 3 and the conveying tube 9 has been fully inserted into the container 3.

In the delivered state shown in FIG. 3, i.e., with the container 3 (still) closed, the nebulizer 1 can be put into storage. In particular, the closed seal 24 ensures that any solvent contained in the fluid 2 cannot escape or in any case can only escape in very tiny amounts.

To prevent unwanted opening of the container 3, particularly the seal 24 or the vent opening 26, in the delivered state of the nebulizer 1, the nebulizer 1 preferably has a transportation lock (not shown in the first embodiment). By frictional, forcible or interlocking engagement, for example, the transportation lock prevents the container 3 from undesirably moving axially in the nebulizer 1, e.g., during transportation, in the event of accidental dropping of the nebulizer 1 or the like, and thereby accidentally coming open. Some possible was of securing the container 3 in transit are described in more detail with reference to other embodiments.

It is noted that the opening of the container 3 is preferably carried out exclusively by mechanical means and/or manual actuation. However, it is additionally or alternatively possible to open it in other ways, e.g., by chemical, electrical, magnetic, pneumatic, hydraulic or similar means.

The proposed nebulizer 1 is activated after the removal of the securing member 27 and (total) axial pushing on of the housing part 18, and can be used in the same way as the nebulizer 1 shown in FIGS. 1 & 2. As previously the nebulizer had to be opened by removing the housing part 18, putting in the container 3 and then closing the nebulizer 1 by pushing on the housing part 18, the process is now easier to carry out and more reliable in operation. In particular, it prevents the wrong container 3 or used containers 3 from being inserted in the nebulizer 1 by the user. Additionally, it ensures that a separately supplied container 3 is not accidentally opened before being inserted in the nebulizer 1. Additionally, the proposed solution prevents possible soiling or damage to the nebulizer 1, e.g., the conveying tube 9 or the like, when the nebulizer 1 is opened and the container 3 is used improperly.

As preferably the container 3 cannot then be removed, especially because the nebulizer 1 cannot be opened and the housing part 18 cannot be removed again, undesirable replacement of the container 3 by the user, and in particular, undesirable interim or subsequent opening of the nebulizer 1 by the user can be prevented.

The other embodiments will now be described in more detail with reference to FIGS. 5 to 35. The relevant explanations are restricted to essential differences from the first embodiment mentioned above and from the known nebulizer 1 according to FIGS. 1 & 2. The remarks and explanations given regarding the first embodiment and the known nebulizer 1 thus apply accordingly or in supplementary fashion, even if they have not been repeated, for reasons of simplicity.

Figure 7:
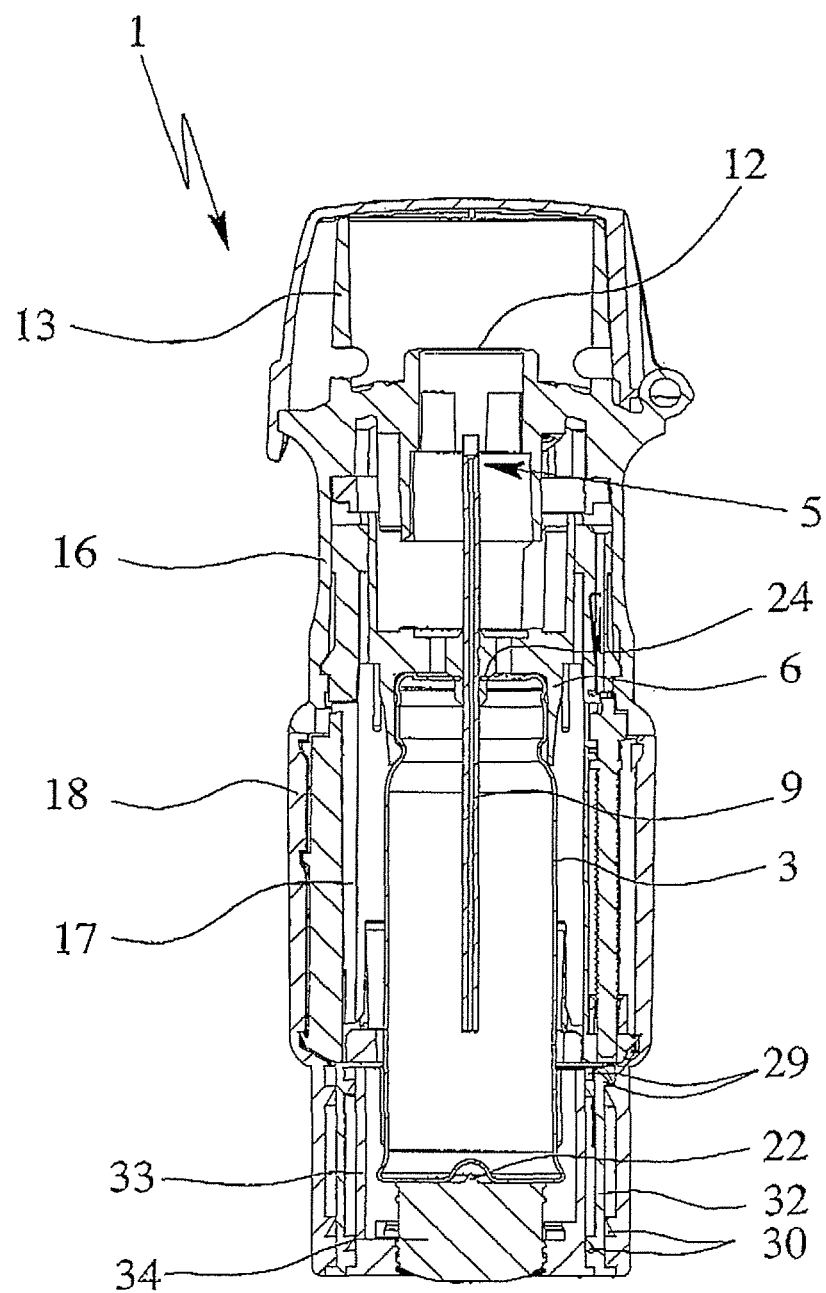
FIG. 7 is a schematic section through the nebulizer according to FIG. 5 in the activated state or with the container open.

FIGS. 5 to 7 show a second embodiment of the proposed nebulizer 1. FIG. 5 shows the nebulizer 1 in the delivered state, i.e., with the container 3 inserted therein but still sealed. FIG. 6 shows a magnified detail from FIG. 5. FIG. 7 shows the nebulizer 1 in the activated state, i.e., with the container 3 open.

In the second embodiment the nebulizer 1, preferably the housing member 18 is of telescopic construction and can be pushed together or axially shortened. In particular, the housing part 18 according to the second embodiment comprises two axially insertable telescopic parts 32, 33 and an axially insertable base part 34.

FIG. 5 shows the nebulizer 1 or the housing part 18 in the telescopically extended, non-activated state. In this state, the 2 telescopic parts 32, 33 and the base part 34 are preferably secured against unwanted axial insertion by means of latching engagements and/or a frictional securing. In particular, the forces required or having to be overcome for the axial insertion are matched to one another such that when axial pressure is applied to the base part 34, initially, the first telescopic part 32 is pushed into the housing part 18, then the second telescopic part 33 is pushed into the first telescopic part 32 and finally the base part 34 is pushed axially into the second telescopic part 33.

FIG. 7 shows the axially pushed-in activated state. In this state, the telescopic parts 32, 33 and the base part 34 are preferably axially secured in their axial positions by latching engagement, frictional locking or, in particular, interlocking engagement.

For example, for axially securing the telescopic parts 32, 33 relative to the housing part 18, corresponding latching lugs 29 engage in latching recesses 30, 31 in order to obtain the desired securing in the axially extended position, on the one hand, and in the axially pushed-in position, on the other hand.

The magnification of a detail of FIG. 5 shown in FIG. 6 illustrates a transportation lock 36 for the nebulizer 1 for axially securing or fixing the container 3 in the delivered state of the nebulizer 1. In the embodiment shown the transportation lock 36 has an encircling retaining bead or at least one retaining arm 37. The retaining bead or retaining arm 37 co-operates with the radially somewhat widened container base 21 such that the container 3, in the delivered state, is securely held in an axially defined manner on an annular shoulder or an annular flange 38 or some other abutment.

In the delivered state, in the embodiment shown, the base part 34 is secured in the telescopically or axially extended position by at least one radial projection or encircling bead 35 which engages radially behind complementary structures on the telescopic part 33. These securing forces can only be overcome by the application of sufficiently forceful axial pressure, for example, as a result of plastic or elastic deformation and/or radial yielding of the projections/beads 35. During the subsequent axial pushing in of the base part 34 relative to the telescopic part 33, the piercing element 22 preferably provided on the base part 34 pierces the vent opening 26 and opens it up. In addition, the base part 34 comes into contact with the container base 21 and forces the container 3 axially out of the transportation lock 36 and presses it with the container head against or into the holder 6 in the nebulizer 1 (with the nebulizer 1 under tension). Thus, the axial retaining force of the transportation lock 36 is overcome by means of the base part 34. In particular, the retaining bead or retaining arm 37 is constructed to be sufficiently elastically or plastically deformable in the radial direction for this purpose.

After the base part 34 has been pushed fully into the second telescopic part 33, the base part 34 is preferably secured again against axial displacement or outward movement by radial engagement and/or frictional engagement with the telescopic part 33.

Figures 8, 9:
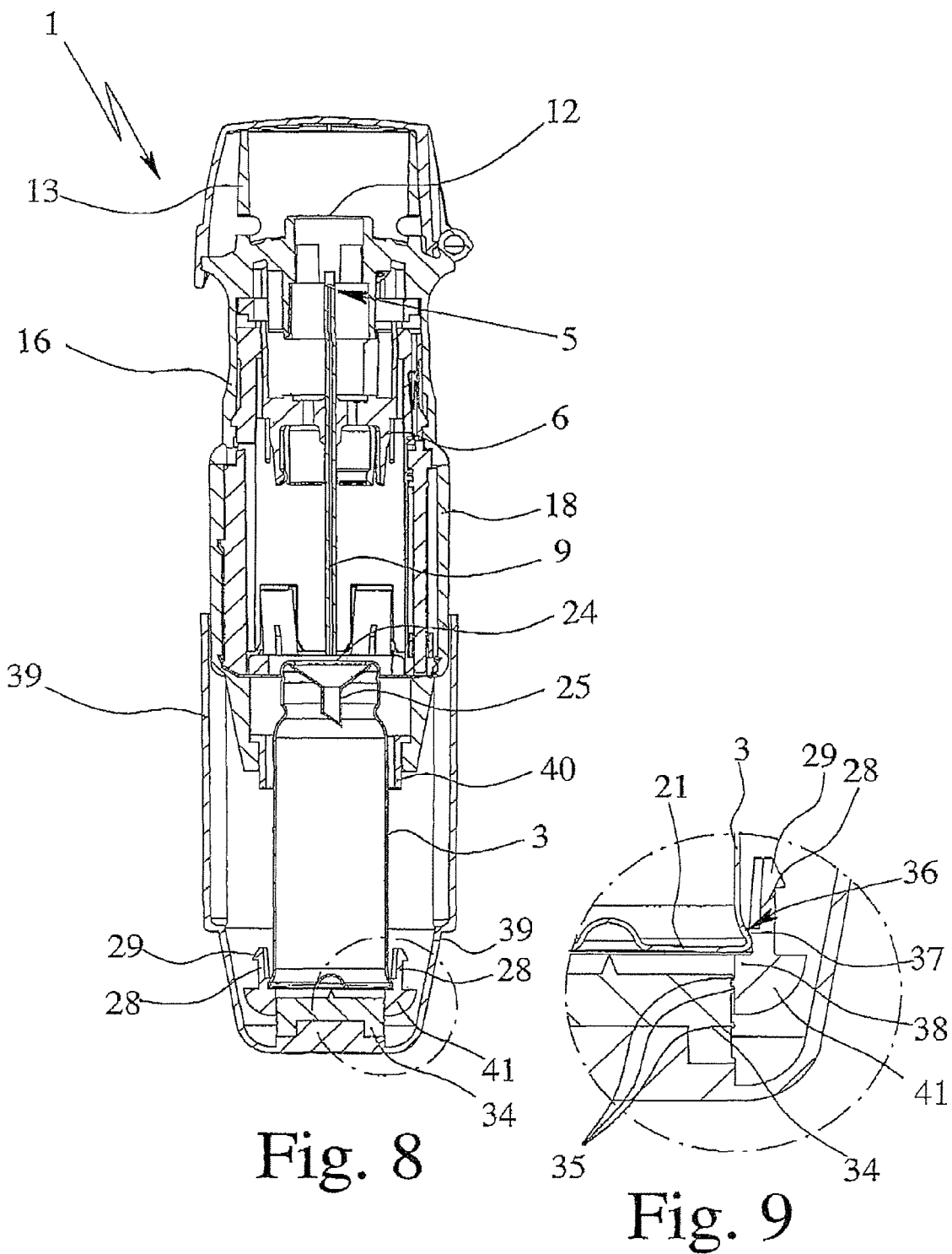
FIG. 8 is a schematic section through a proposed nebulizer according to a third embodiment in the delivered state with a sealed container incorporated therein.
FIG. 9 shows the broken line encircled detail from FIG. 8 in an enlarged view.
Figure 10:
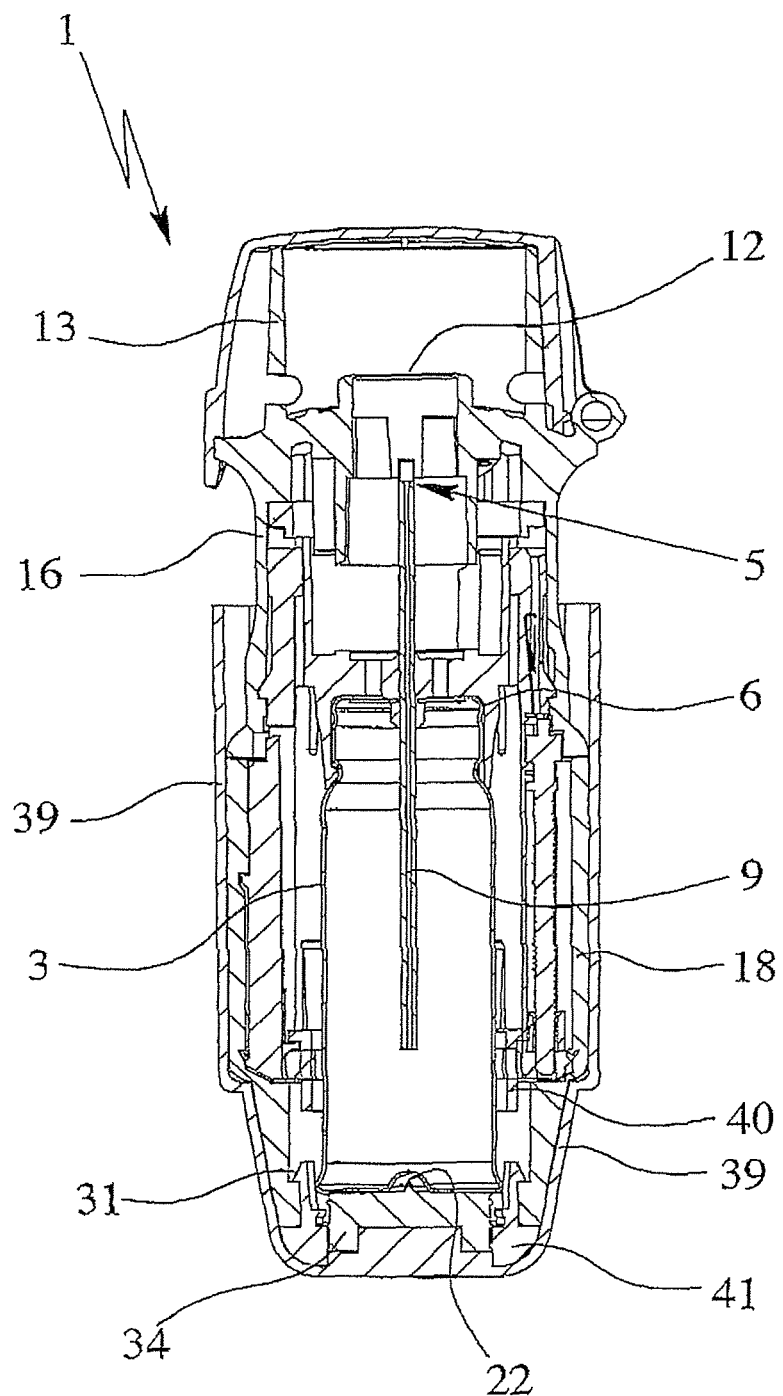
FIG. 10 is a schematic section through the nebulizer according to FIG. 8 in the activated state or with the container open and with an actuating member pushed onto it.
Figure 11:
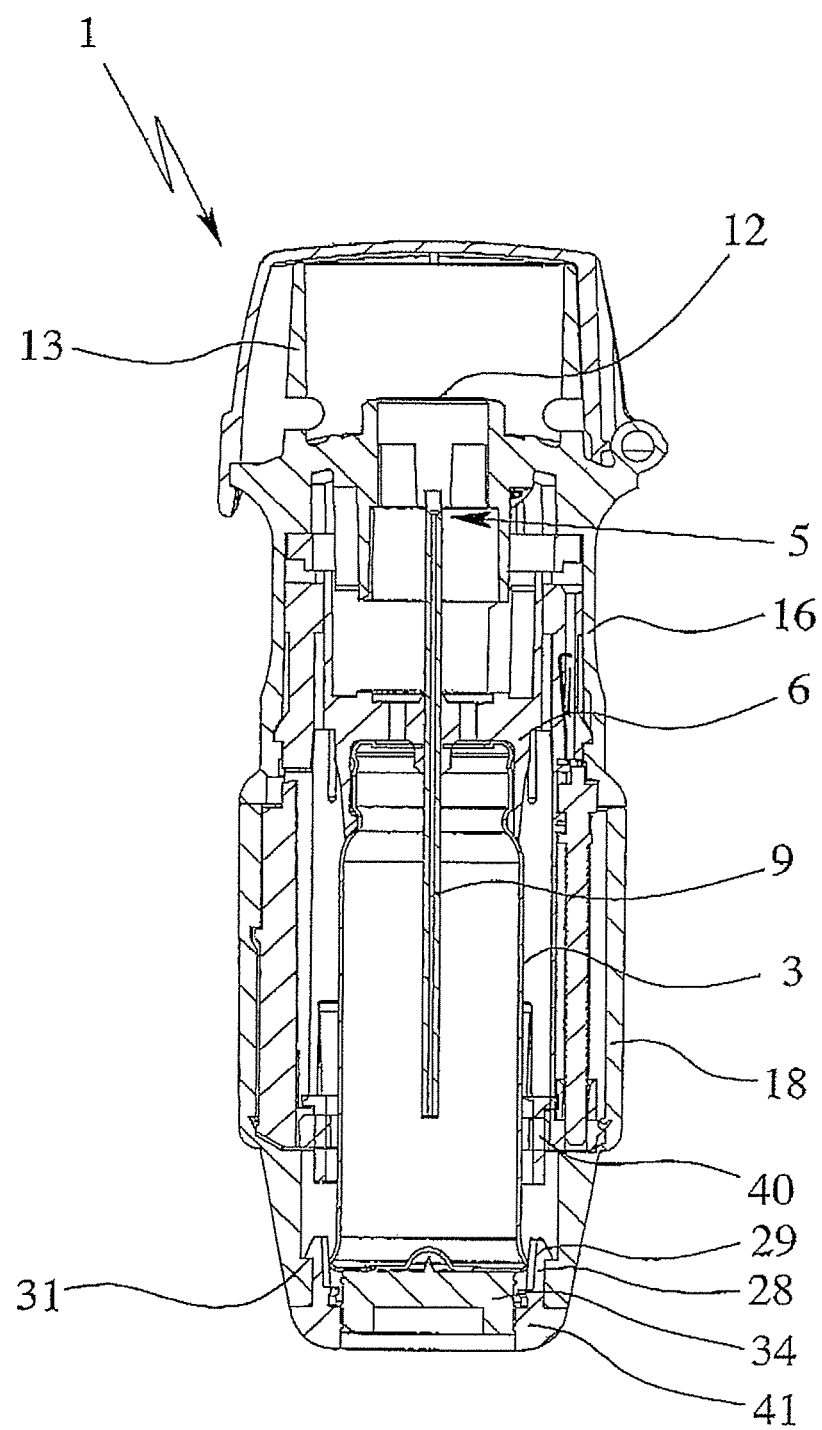
FIG. 11 is a nebulizer according to FIG. 10 without the actuating member.
Figure 12:
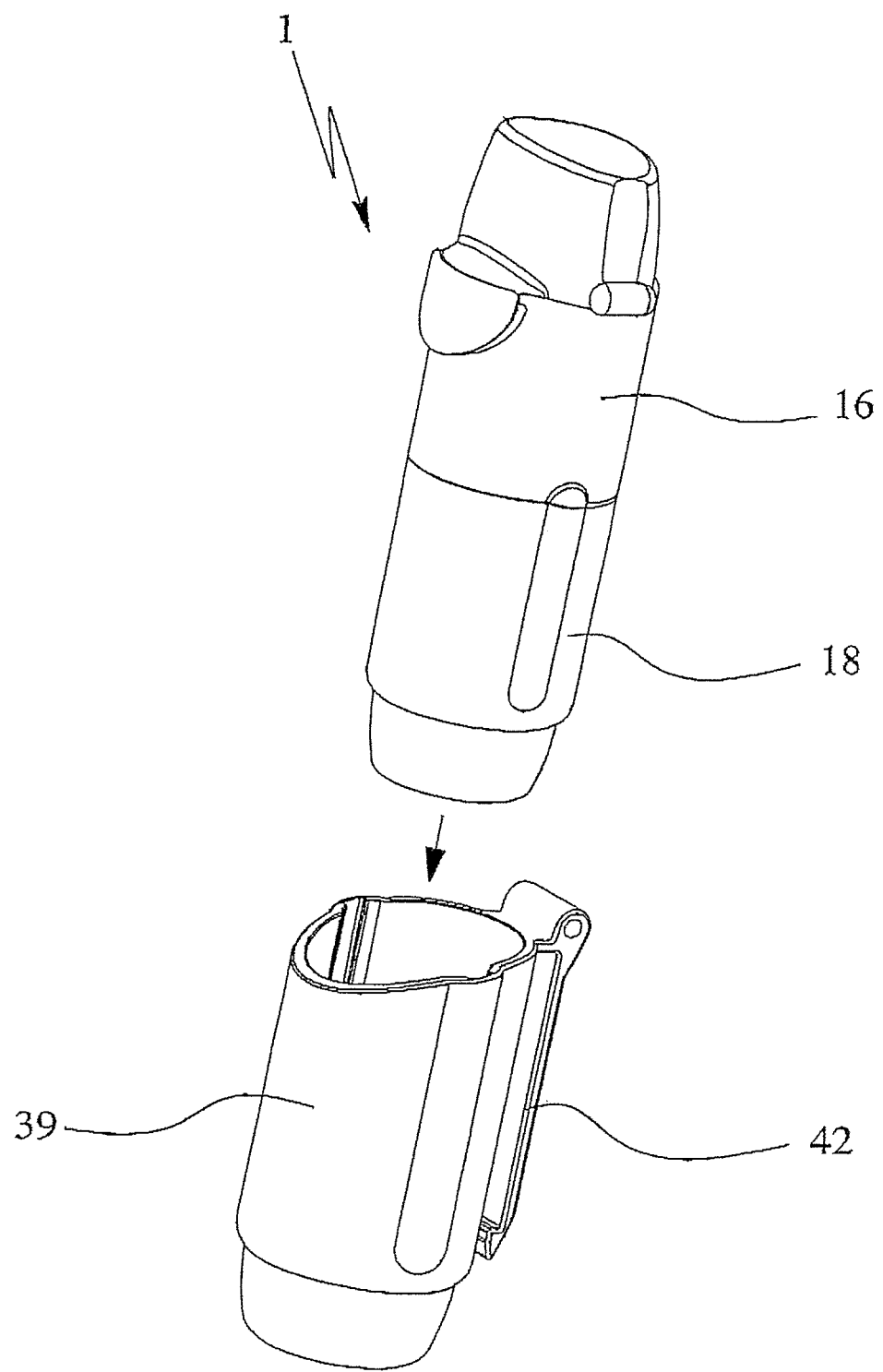
Figure 13:
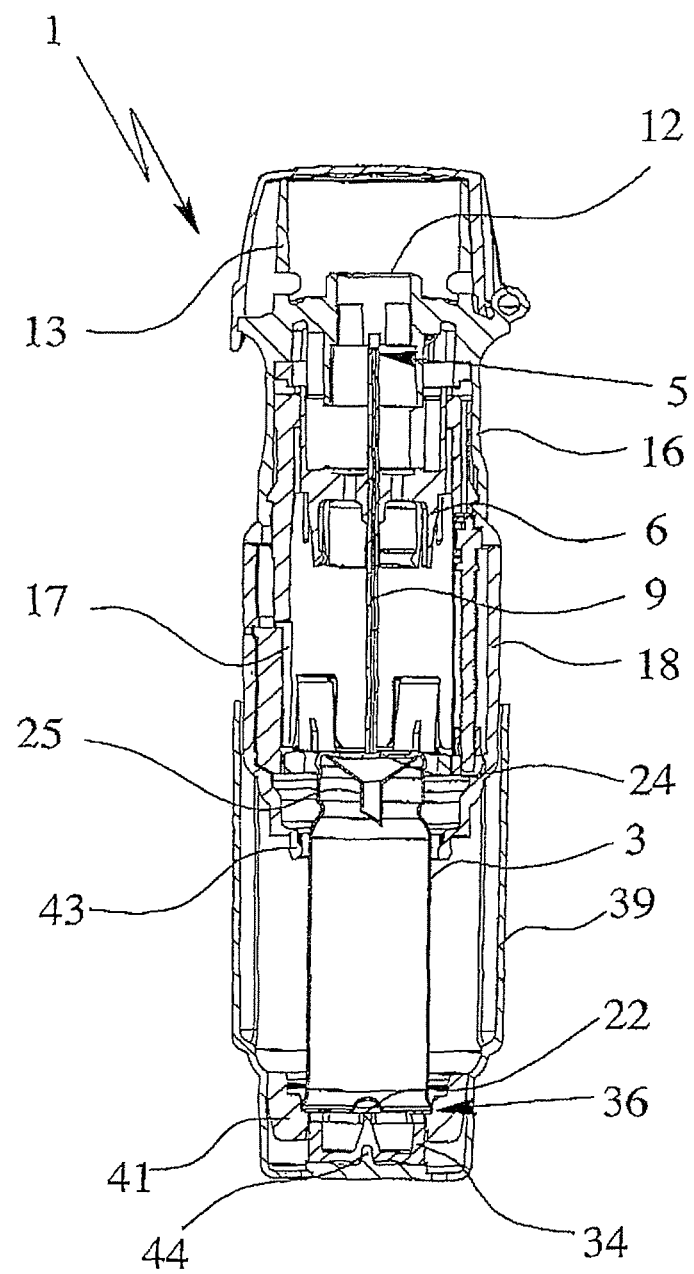
FIG. 13 is a schematic section through a proposed nebulizer according to a fifth embodiment in the delivered state with a sealed container incorporated therein.
Figure 14:
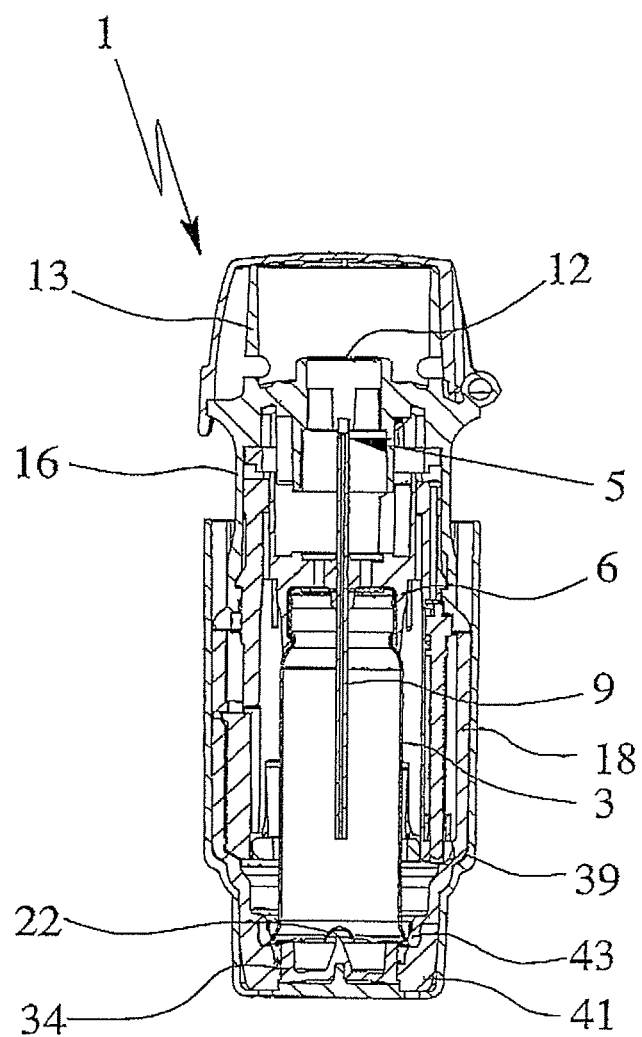
FIG. 14 is a schematic section through the nebulizer according to FIG. 13 in the activated state or with the container open.

FIGS. 8 to 11 show a third embodiment of the proposed nebulizer 1. FIG. 8 shows the nebulizer 1 in the delivered state with the container 3 sealed. FIG. 9 shows a magnified partial view from FIG. 8. FIG. 10 shows the nebulizer 1 in the activated state, i.e., with the container 3 open. FIG. 11 shows the nebulizer 1 in the activated state as in FIG. 10, but without an actuating member 39.

In the second embodiment, in addition to the housing part 18, the nebulizer 1 comprises an actuating member 39 which is preferably in the form of a cap, quiver or cup. The actuating member 39 is only partially fitted or pushed onto the housing part 18 in the delivered state and holds the container 3 axially at a distance from the conveying tube 9 in the nebulizer 1, as shown in FIG. 8. The housing part 18 is accordingly constructed to be open at its base.

Optionally, a guide sleeve 40 for radially guiding the container 3 is arranged in the region of the base opening in the housing part 18. The guide sleeve 40 projects axially beyond the end of the housing part 18, particularly in the delivered state, and can be pushed axially into the housing part 18 on activation by pushing the actuating member 18 (fully) in the axial direction. Depending on the configuration of the housing part 18, particularly depending on the degree of radial play with the container 3, the guide sleeve 40 may also be omitted.

The base part 34 with the piercing element 22, as in the second embodiment, and an insertion part 41 are preferably mounted in the actuation member 39.

The insertion part 41 is constructed in a similar manner to the second telescopic part 33 according to the second embodiment. As can be seen from the magnified detail shown in FIG. 9, the base part 34 and the insertion member 41 engage radially behind one another, as already explained with reference to the second embodiment in the relationship between the second telescopic part 33 and the base part 34, and reference is therefore made to the remarks made at that point. The insertion member 41 also forms a transportation lock 36, as already described in connection with the second embodiment, and reference is therefore made to the explanations given there.

In the delivered state, the base part 34 is held axially by preferably radial engagement and/or frictional locking by the actuating member 39. The base part 39, in turn, holds the insertion member 41 axially and this, in turn, axially secures the container 3 via the transportation lock 36.

To activate the actuating member 39, it is pushed fully onto the housing part 18 in the axial direction until the actuating member 39 receives or encloses the nebulizer 1 and particularly the housing part 18, preferably in the manner of a cap or hat, as shown in FIG. 10.

During the axial pushing on of the actuating member 39, the container 3 is, first of all, pushed onto the conveying tube 9, i.e., it is opened by the conveying tube 9.

The further pushing of the actuating member 39 onto the housing part 18 causes the insertion member 41 to come into engagement with the housing part 18, and in particular, latching arms 28 with latching lugs 29 engage in corresponding latching recesses 31 in the housing part 18 and thereby secure the insertion member 41 axially to the housing part 18.

In the course of the last part of the axial movement, the base part 34 is finally pressed axially into the insertion part 41, as a result of which the piercing element 22 pierces or opens up the vent opening 26 and the base part 34 axially released the container 3 from the transportation lock 36 and—with the nebulizer 1 or pressure generator 5 under tensio—presses it axially towards or into the holder 6 in order to bring the holder 6 into engagement with the container 3. This position is shown in FIG. 10.

In the fully pushed-on state, as shown in FIG. 10, the nebulizer 1 can be used by means of the actuating member 39. In particular, the nebulizer 1 or its pressure generator 5 can be tensioned in the usual way by rotating the actuating member 39 accordingly.

However, the actuating member 39 is not needed for (further) use of the nebulizer 1. Rather, depending on the design of the nebulizer 1, the actuating member 39 can or must be removed again after the activation (full insertion), and in particular must be pulled away axially. Preferably, the nebulizer 1 is constructed such that the axial detachment or removal of the actuating member 39 is only possible after previously being pushed fully onto the housing part 18 or after activation of the nebulizer 1. A suitable locking or release mechanism may be provided for this purpose, but is not shown here.

FIG. 12 shows in a schematic exploded view a fourth embodiment of the proposed nebulizer 1. In this alternative embodiment, which is similar to the third embodiment, the actuating member 39 can be used to secure the nebulizer 1 and for this purpose has a preferably clip-like resilient holding bar or holding clip 42 or the like on the outside. The actuating member 39, and hence the nebulizer 1, if necessary, can be attached to a belt, waistband, pocket or the like by means of the retaining bar or clip 42.

As in the third embodiment the actuating member 39 can be removed from the nebulizer 1 as necessary—once the nebulizer 1 has been activated or the container 3 has been opened. In particular, the actuating member 39 according to the fourth embodiment can be used as necessary to secure the nebulizer 1, as desired. In order to obtain the optimum securing of the nebulizer 1, the actuating member 39 is preferably releasably connectible to the nebulizer 1 by clamping and/or latching, and in particular, the nebulizer 1 can be inserted in a preferably at least substantially hollow cylindrical portion of the actuating member 39.

The construction and use of the actuating member 39 as a holder for the nebulizer 1 can also be designed irrespective of the preinstalled container 3, i.e., in general for any type of nebulizer 1. Other constructions are then possible, in particular; for example, the actuating member 39 may be merely clamped to the nebulizer 1.

FIGS. 13 & 14 are schematic sections illustrating a fifth embodiment of the proposed nebulizer 1. FIG. 13 shows the nebulizer 1 in its delivered state (with a preinstalled sealed container 3). FIG. 14 shows the nebulizer 1 in the activated state, i.e., with the container 3 open.

The fifth embodiment is substantially similar to the third embodiment. The nebulizer 1 can be activated by pushing on the actuating member 39 which is preferably cap-, quiver- or cup-shaped. Only essential differences between this and the third embodiment will be described hereinafter.

The insertion member 41 is not provided with latching arms 28, but for fitting onto the housing part 18, it is preferably in the shape of a hat, quiver, cup or cap. In the activated state, the insertion member 41 sits around or over an annular portion 43 which is formed in the region of the free end of the housing part 18, and in particular, surrounds or forms the through-opening for the axial insertion of the container 3. In particular, the insertion member 41 is connected to the housing part 18 axially in frictional or interlocking engagement in the activated state.

Preferably, the insertion member 41, as in the third embodiment, forms the smoothest possible outer contour in the activated state or when connected to the housing part 18 so as to give the nebulizer 1 a pleasant surface feel and ease of handling even with the actuating member 39 removed. In accordance with the third embodiment, the actuating member 39 in the fifth embodiment can, in fact, be fully removed or axially pulled off after activation as well.

In the fifth embodiment, the nebulizer 1 may comprise the guide sleeve 40 according to the third embodiment for radially centring or securing or supporting the container 3 in the delivered state, particularly in order to be able to prevent unwanted detachment from the transportation lock 36 by tilting the container 3 to one side. However, no guide sleeve 40 is provided in the embodiment shown. Instead, the through-opening for the container 3 is formed at the free axial end of the housing part 18 or is provided with slight radial play relative to the container 3, for example in the region of the annular portion 43, such that there is no need for a separate component such as the guide sleeve 40.

Another constructional difference between the third embodiment and the fifth embodiment is that, in the fifth embodiment, the base part 34 is held axially by the actuating member 39, as an alternative or in addition to the radial clamping in the delivered state, as show in FIG. 13. Preferably, for this purpose, the actuating member 39 engages axially with a preferably nipple-, pin- or bolt-shaped projection 44 in a corresponding recess in the base of the base part 34, so that the base part 34 is axially secured to the actuating member 39.

In the activated state, the actuating member 39 can be released from the base part 34 to allow the actuating member 39 to be removed axially if necessary. Preferably, the interlocking or frictional engagement and the material forces are designed such that the base part 34 is held by the insertion member 41 in the pressed-in or retracted piercing position shown in FIG. 14, even when the actuating member 39 is pulled away axially. For example, when the actuating member 39 is pulled away axially, the projection 44 is broken off and remains on or in the base part 34.

The construction of the transportation lock 36 and the release of the container 3 from the transportation lock 36 during activation preferably correspond to the third embodiment. Preferably, activation takes place even with the nebulizer 1 or pressure generator 5 under tension, so that when the actuating member 39 is pushed fully on in the axial direction the container 3 is not only opened and pierced at its base by the insertion of the conveying tube 9 but is also brought into engagement at the head end with the holder 6.

FIGS. 15 & 16 show diagrammatic sections through a sixth embodiment of the proposed nebulizer 1. FIG. 15 shows the nebulizer 1 in the delivery position. FIG. 16 shows the nebulizer 1 in the activated position, i.e., ready for use with the container 3 open.

In the sixth embodiment, in a similar manner to the third embodiment, an insertion member 41 and a base part 34 are provided which can be inserted for activation into the correspondingly axially open housing part 18. In contrast to the third embodiment, a separate or additional actuating member 39 is not needed. Instead, the insertion member 41 is constructed in the manner of a sleeve and is guided or held by a hollow cylindrical portion 45 which is formed, particularly molded, on the housing part 18, especially in the delivered state and during the axial insertion into the nebulizer 1 or the housing part 18. In the pushed-in or activated state, the insertion part 41 together with the base part 34 terminates the hollow cylindrical portion 45, thus forming an at least substantially smooth outer contour for the nebulizer 1.

In the sixth embodiment, the base part 34 is held by the insertion member 41, preferably in a defined manner by radial engagement in an axial position in which the piercing element 22 is axially spaced from the base seal, i.e., the vent opening 26 in the container 3.

To activate it, pressure is applied to the base part 34. As a result, the base part 34 is inserted or pushed axially (further) into the insertion part 41, as a result of which the piercing element 22 pierces or opens the vent opening 26. At the same time, beforehand or afterwards, the insertion member 41 with the container 3 essentially arranged therein is pushed into the nebulizer 1 or housing part 18, and as a result, the conveying tube 9 is axially inserted in the container 3 and the container 3 is thus opened. With the nebulizer 1 or pressure generator 5 under tension, the container 3 is finally brought into engagement with the holder 6 at the head end. In the pushed-in activated position shown in FIG. 16, the insertion member 41 and the base part 34 are preferably secured in axially latching and/or clamping manner on the housing part 18 or hollow cylindrical section 45.

Figure 15:
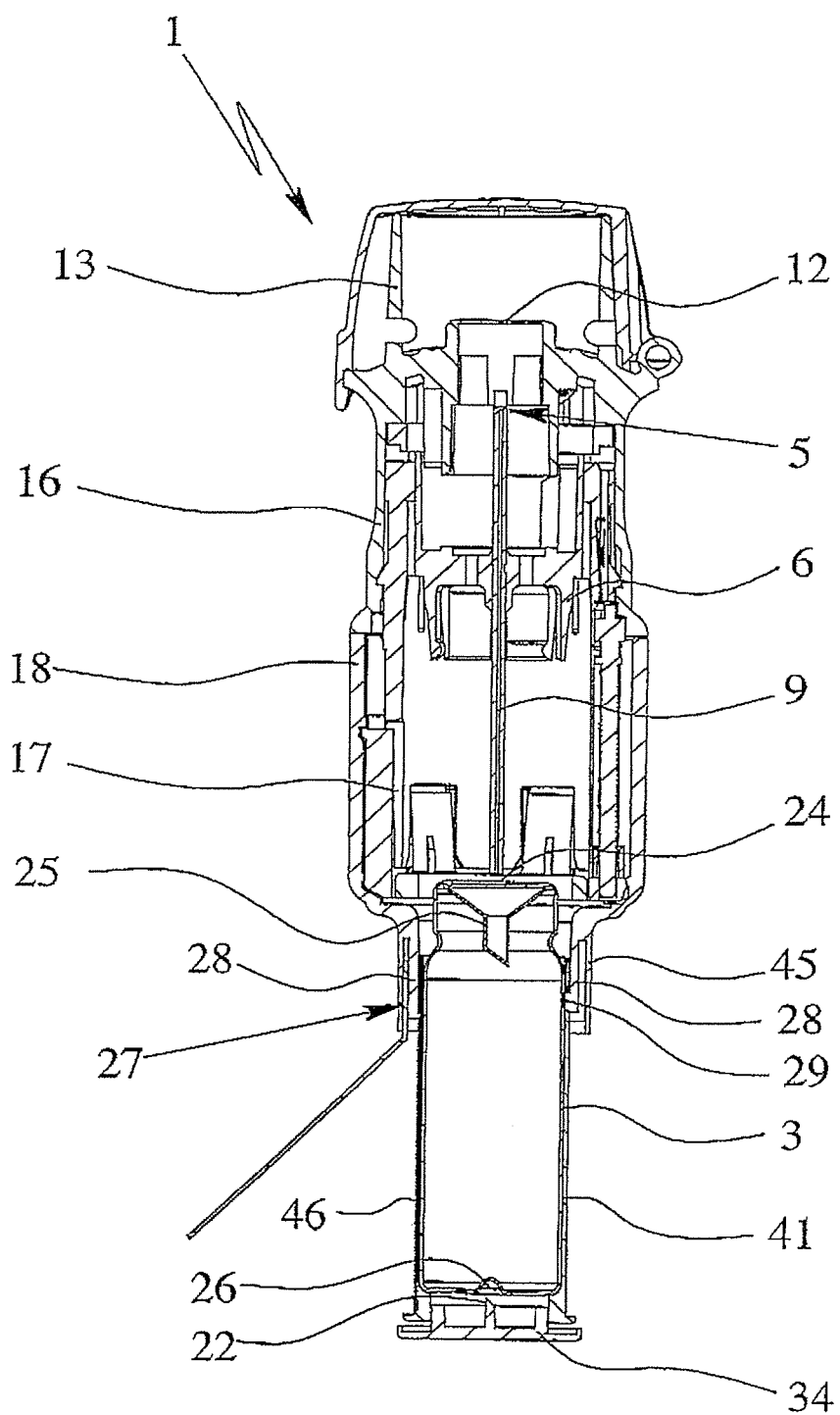
FIG. 15 is a schematic section through a proposed nebulizer according to a sixth embodiment in the delivered state with a sealed container incorporated therein.
Figure 16:
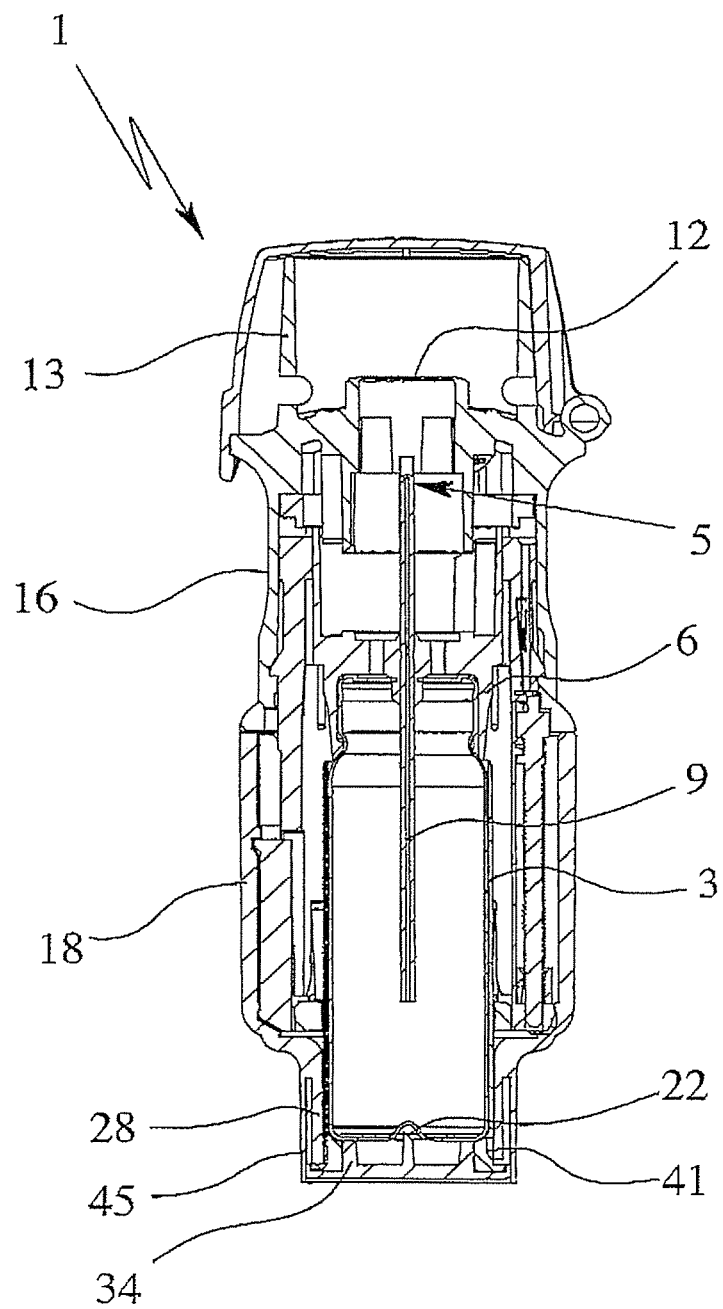
FIG. 16 is a schematic section through the nebulizer according to FIG. 15 in the activated state or with the container open.

To prevent unwanted withdrawal of the insertion member 41 during insertion, e.g., from a half-inserted position or from the fully inserted position, the nebulizer 1 according to the sixth embodiment preferably comprises a progressive, preferably saw tooth-like latching 46 or the like between the housing part 18 and the insertion member 41 so that the insertion member 41 is only axially insertable but cannot be axially withdrawn in the opposite direction. In the embodiment shown, the latching 46 is formed on the outside in a longitudinal direction over a sleeve portion of the insertion member 41. Then, at least one latching arm 28 arranged on the nebulizer 1, particularly on the housing part 18 in the hollow cylindrical section 45, engages in the latching member 46. FIGS. 15 & 16 show two axially extending latching arms 29 which are elastically biased in the radial direction towards the insertion member 41.

To form a transportation lock to prevent accidental pushing in of the insertion member 41 in the delivered state of the nebulizer 1, according to the sixth embodiment, a securing member 27 is preferably provided in the form of or comprising a safety tag, as show in FIG. 15. The safety tag is, for example, arranged or inserted radially on the outside between at least one latching arm 28 and a wall of the hollow cylindrical section 45, in order to block at least one latching arm 28 or several or all of the latching arms 28 against radially springing out and thereby to prevent the axial movement inwards of the insertion member 41. Only after the removal, particularly the axial withdrawal of the safety tag, are the latching arm or latching arms 28, and hence the latching member 46, released so that the insertion member 41 is able to be axially pushed in and the nebulizer 1 thereby activated.

Figure 17:
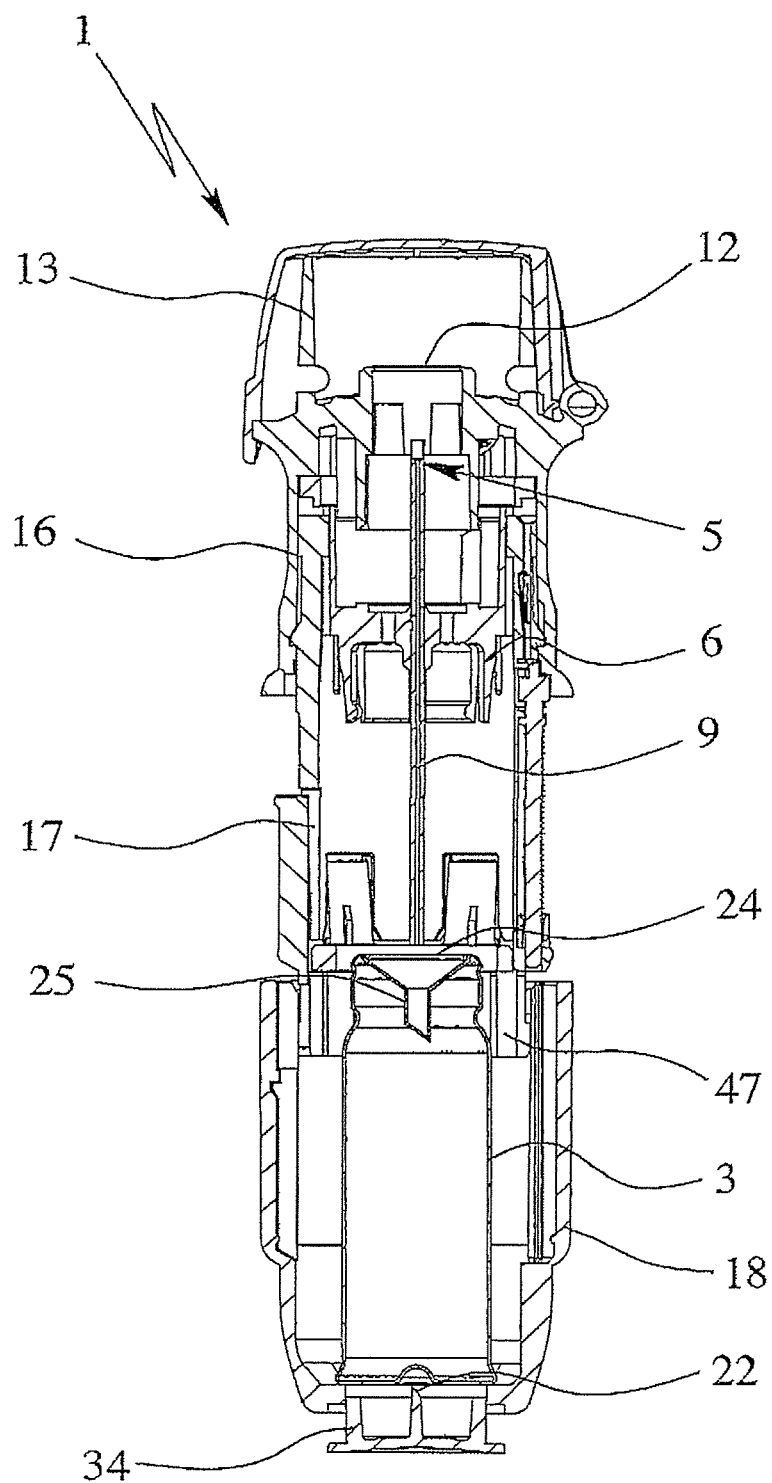
FIG. 17 is a schematic section through a proposed nebulizer according to a seventh embodiment in the delivered state with a sealed container incorporated therein.
Figure 18:
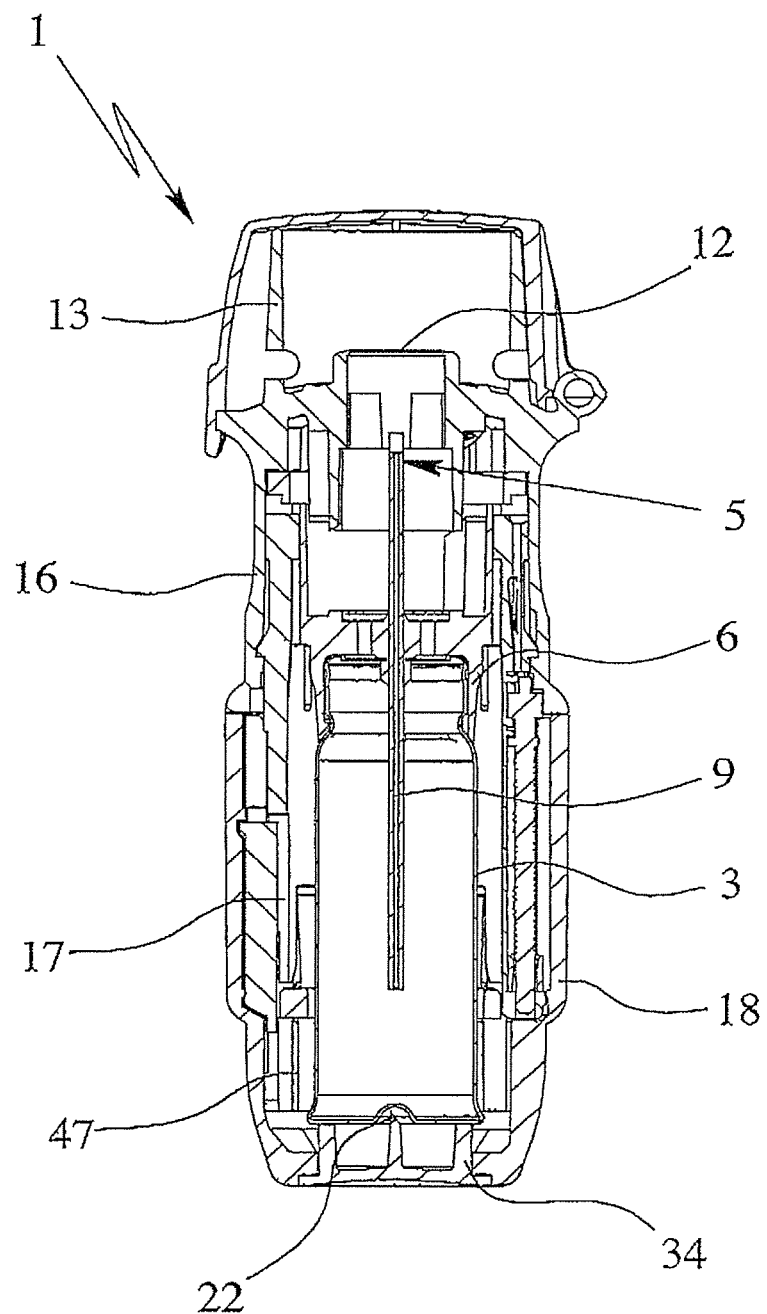
FIG. 18 is a schematic section through the nebulizer according to FIG. 17 in the activated state or with the container open.
Figure 19:
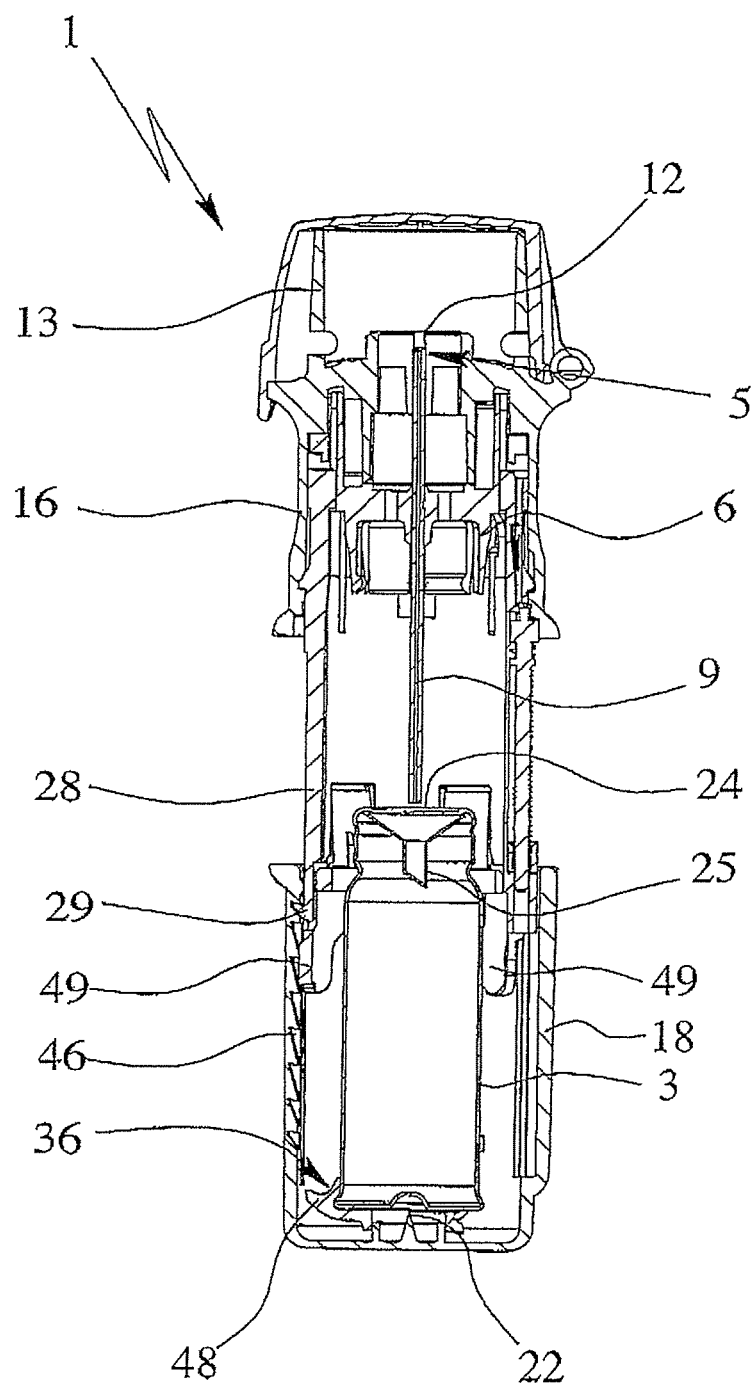
FIG. 19 is a schematic section through a proposed nebulizer according to an eighth embodiment in the delivered state with a sealed container incorporated therein.

FIGS. 17 & 18 show schematic sections through a seventh embodiment of the proposed nebulizer 1. FIG. 17 shows the nebulizer 1 in the delivered state. FIG. 18 shows the nebulizer 1 in the activated state.

The seventh embodiment is very similar to the sixth embodiment. However, in the sixth embodiment, no insertion member 41 is provided. Instead, in the delivered state, the housing part 18 is axially pushed only partially onto the nebulizer 1, particularly the inner part 17 or a retaining portion 47 provided thereon. The retaining portion 47 is provided, for example, in the lower part 17*b* of the inner part 17. The retaining portion 47 is axially extended beyond the end of the inner part 17 to enable the housing part 18 to be held in a sufficiently axially displaced position in the delivered state so that the container 3, preinstalled in the housing part 18, is still axially spaced from the conveying tube 9. Preferably, by means of a suitable engagement, latching or similar, the housing part 18 can no longer be axially withdrawn or removed once it has been axially (partially) pushed onto the retaining portion 47.

The housing part 18 in the seventh embodiment holds the base part 34 in a manner corresponding or similar to the way in which the insertion member 41 holds the base part 34 in the sixth embodiment. For activation, with the nebulizer 1 or pressure generator 5 preferably under tension, the base part 34 is axially pressed again. As a result the housing part 18 is pushed (fully) onto the nebulizer 1 or the inner part 17 in the axial direction. The container 3 is opened by the axial insertion of the conveying tube 9. Axially pressing the base part 34 into the housing part 18—in particular until the base part 34 is just flush with the axial end of the housing part 18—finally results in the piercing of the base of the container 3, the release of the container 3 from the axial transportation lock 36 at the base, which is formed by the housing part 18 in the seventh embodiment, and axial insertion of the container 3 into the holder 6.

Preferably, between the housing part 18 and the nebulizer 1 or inner part 17, there is provided a device (not shown) such as the latching member 46 in the sixth embodiment having at least one associated latching arm 28 or the like, exclusively to enable the housing part 18 to be pushed onto the nebulizer 1 but prevent axial withdrawal or movement in the opposite direction. According to the sixth embodiment, a securing member 27 (not shown) in the form of or comprising a safety tag or the like may also be provided to prevent the housing part 18 from being pushed in, in the delivered state, if the securing member 27 has not been removed.

FIGS. 19 to 22 show schematic sections through an eighth embodiment of the proposed nebulizer 1. FIG. 19 shows the nebulizer 1 in its delivered state. FIG. 20 shows the nebulizer 1 in the activated state, i.e. with the container 3 already open, but with the nebulizer 1 or pressure generator 5 not yet under tension. FIG. 21 shows the nebulizer 1 in the activated and tensioned state. FIG. 22 shows, in a magnified detail, part of FIG. 21 and illustrates the transportation lock 36 in the eighth embodiment.

In the eighth embodiment, in a similar manner to the seventh embodiment, the housing part 18 is axially pushed on only partly in the delivered state. In contrast to the seventh embodiment, the housing part 18 in the eighth embodiment is closed at its base, i.e., no separate base part 34 is provided. Instead, the piercing element 22 is provided on the inside of the base of the housing part 18, and in the delivered state, the container 3 is held at an axial spacing from the correspondingly constructed transportation lock 36 to prevent opening or piercing of the vent opening 26 at the bottom.

In the example shown, the transportation lock 36 is preferably held in axially movable manner in or by the housing part 18 to allow the base of the container 3 to be pierced on activation.

In the embodiment shown, the transportation lock 36 comprises at least one gripping arm 48, preferably a plurality of gripping arms 48, before axially holding the container 3 in the delivered state by engaging around its preferably radially expanded base end, as show in FIG. 19 for one gripping arm 48.

As in the seventh embodiment, the eighth embodiment preferably comprises a device, such as the latching element 46, having at least one associated latching arm 28 between the housing part 18 and the nebulizer 1 or inner part 17, to allow the housing part 18 only to be pushed axially on but not axially moved back. The latching element 46 is preferably formed on the inside of the housing part 18, as indicated in FIGS. 19 to 21. A latching arm 28 with a latching lug 29 engages in the latching element 46. In contrast to the sixth embodiment, a coarser latching element 46 is provided here. In addition, it is also possible to block the axial pushing-on movement by blocking the latching arm 28 using a securing member 27 (not shown), particularly in the form of or comprising a safety tag or the like.

In the eighth embodiment, the activation is preferably carried out in the untensioned state of the nebulizer 1. After the removal of the safety tag or the like which is optionally provided, the housing part 18 is pushed onto the nebulizer 1, particularly the inner part 17. At the same time, the conveying tube 9 is axially inserted in the container 3 and the container 3 is thus opened.

In the fully pushed-on state, the container 3 is pushed axially further or deeper into the housing part 18, so that the piercing element 22 has pierced or opened the vent opening 26, and the transportation lock 36 is released.

Figure 20:
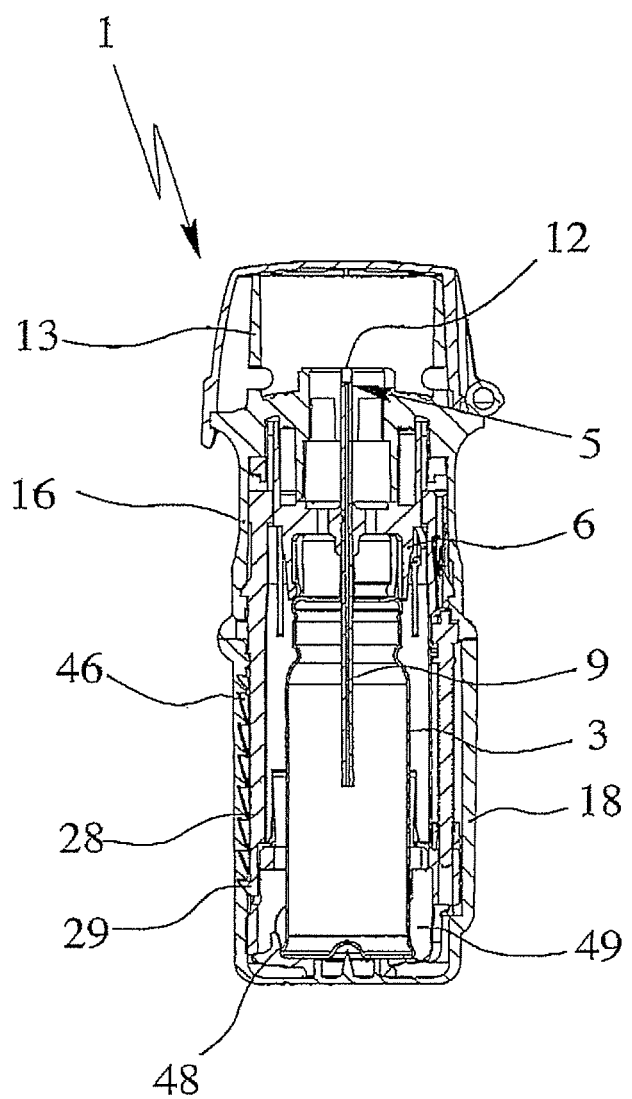
FIG. 20 is a schematic section through the nebulizer according to FIG. 19 in the activated, but untensioned state or with the container open.
Figure 21:
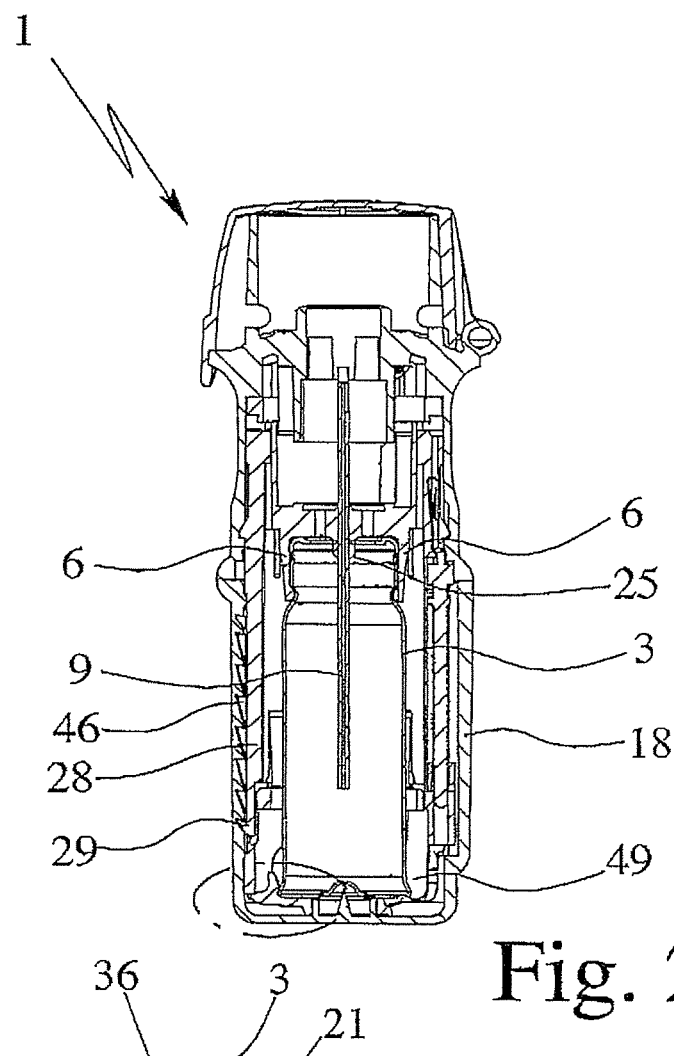
FIG. 21 is a view of the nebulizer corresponding to FIG. 20, but in the tensioned state.
Figure 22:
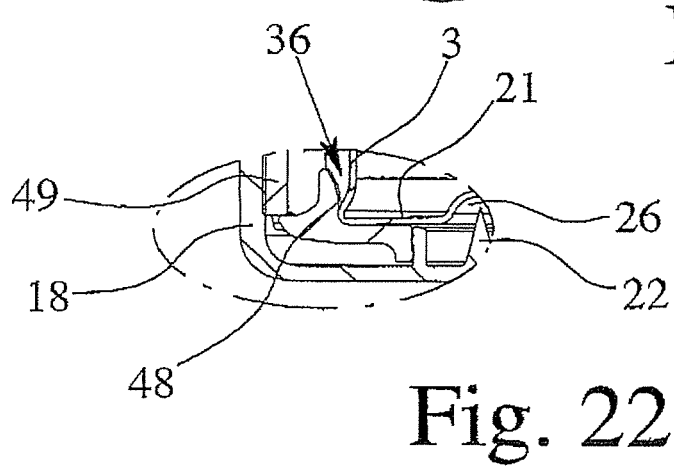
FIG. 22 is an enlarged view of the detail of FIG. 21 enclosed by the dot-dash line.

The transportation lock 36 is opened, in particular, by at least one axial arm or projection 49, which is formed on the inner part 17 or preferably the retaining portion 47. In the embodiment shown a plurality of axial arms 49 corresponding to the gripper arms 48 are provided, which pivot or swing out the gripper arms 48 when the housing part 18 is pushed on fully and thereby open the transportation lock 36, as shown in FIGS. 20 and 21 and particularly in FIG. 22.

Opening the transportation lock 36 or gripper arms 48 preferably requires a force such that first of all the transportation lock 36 is moved axially towards the base of the housing part 18 and as a result the base of the container 3 is opened. This is achieved by correspondingly matching the force ratios between the axial securing of the transportation lock 36 in or on the housing part 18 and the necessary opening force for swiveling the gripper arms 48. Only after the axial end position of the transportation lock 36 in the housing part 18 has been reached are the gripper arms 18 and hence the transportation lock 36 opened in order to release the container 3 axially.

During the subsequent first tensioning, the conveying tube 9 is moved further into the container 3 and the holder 6 is brought into engagement with the container 3. FIG. 21 shows this position. During the subsequent release of the nebulizer 1, the container can be axially moved by the holder 6 in the usual way during the nebulizing process, as the transportation lock 36 remains open and frees the container 3 for axial movement.

Figure 23:
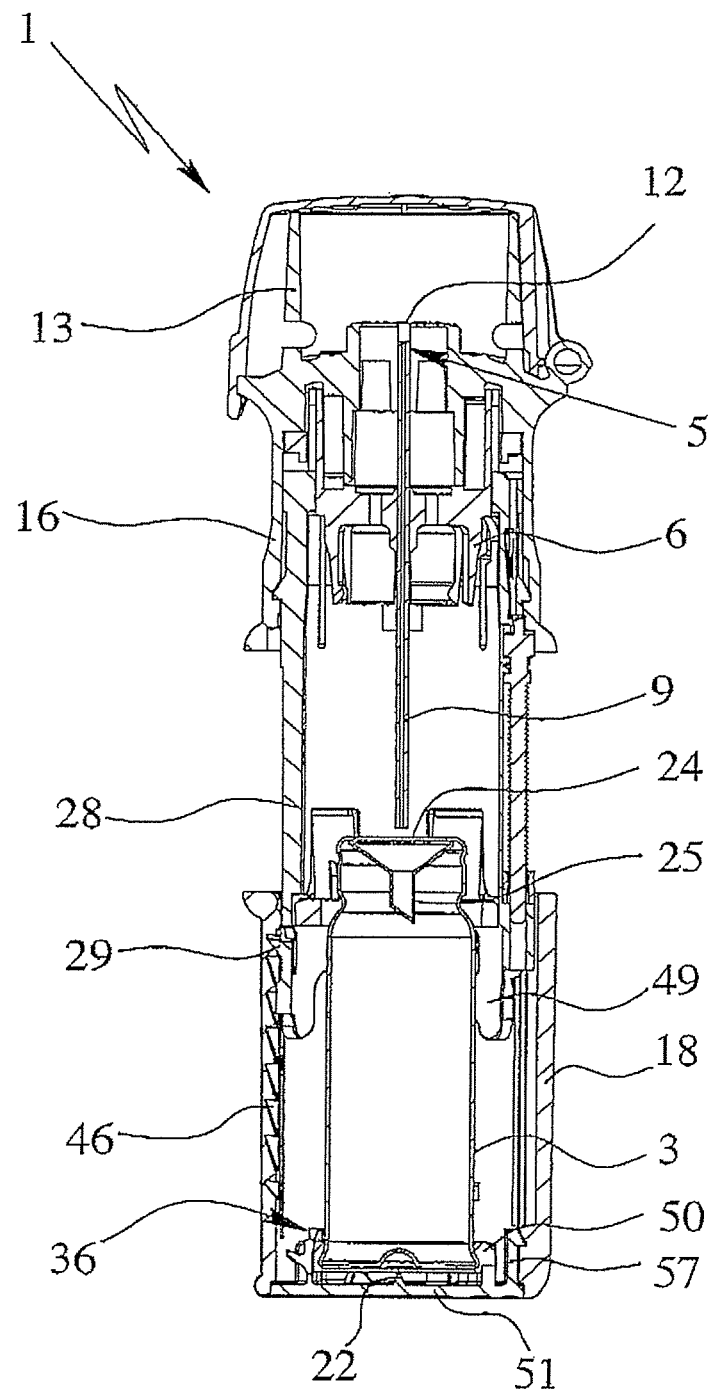
FIG. 23 is a schematic section through a proposed nebulizer according to a ninth embodiment in the delivered state with a sealed container incorporated therein.
Figure 24:
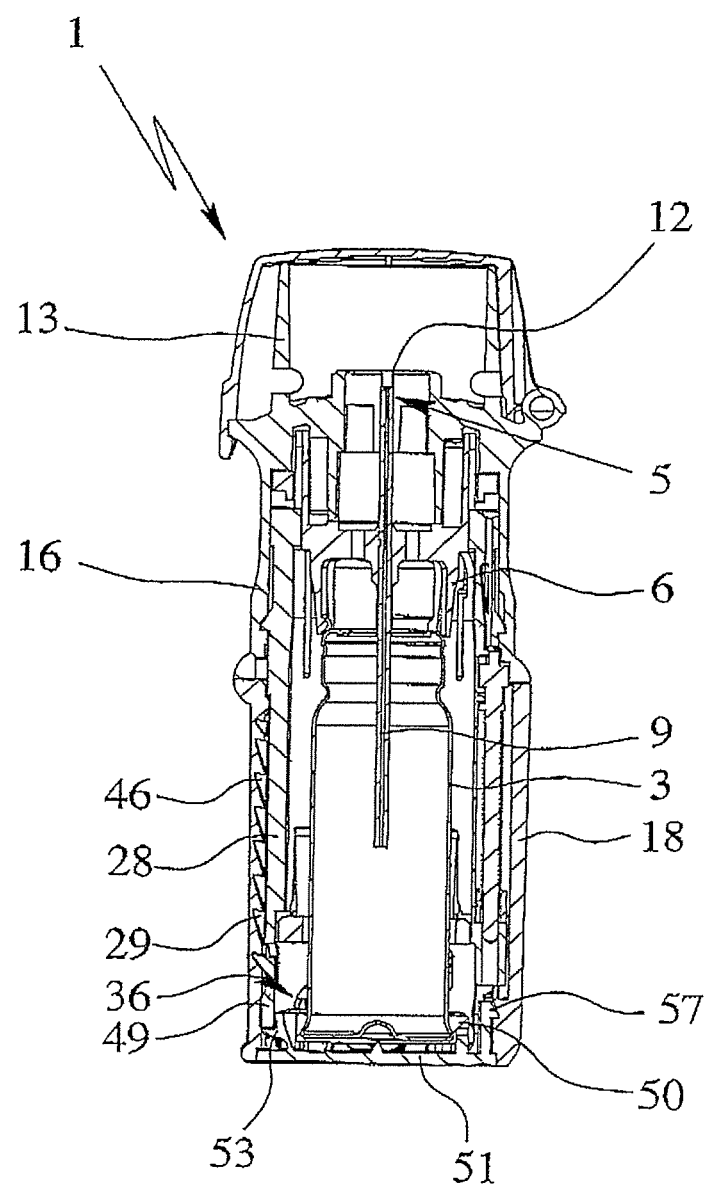
FIG. 24 is a schematic section through the nebulizer according to FIG. 23 in the activated but untensioned state or with the container open.
Figure 25:
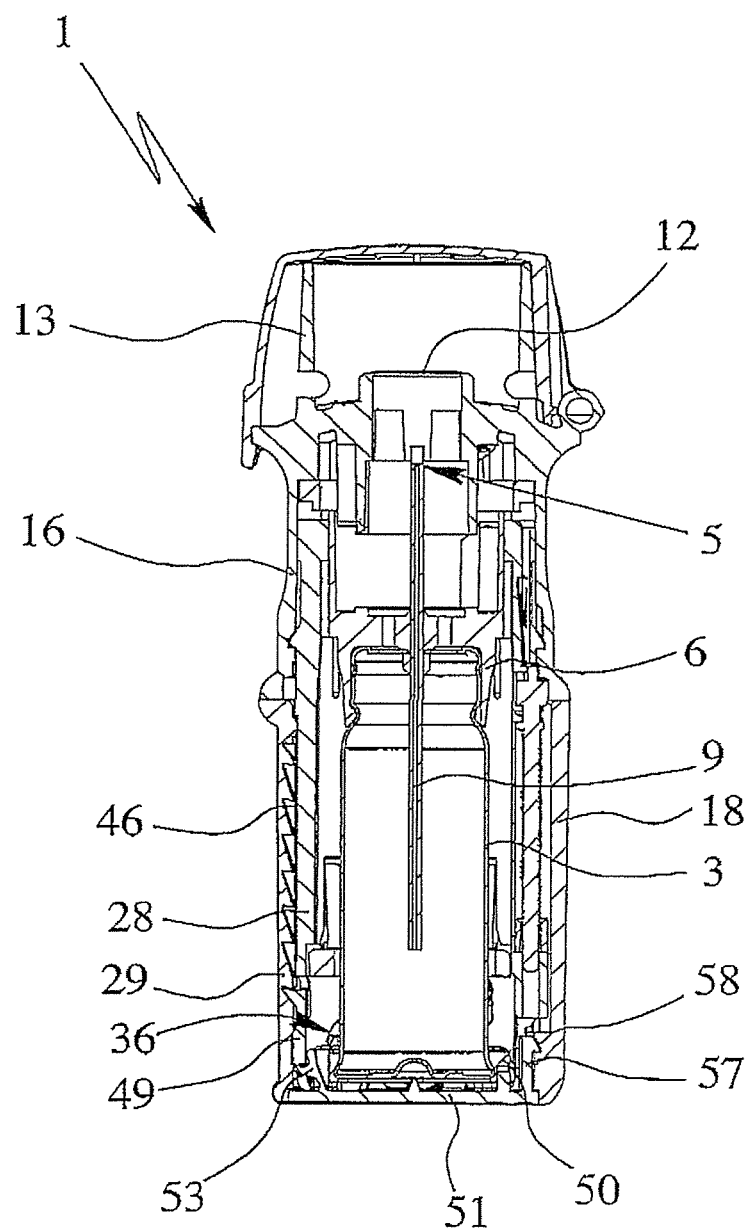
FIG. 25 is a view of the nebulizer corresponding to FIG. 24, but in the tensioned state.
Figure 26:
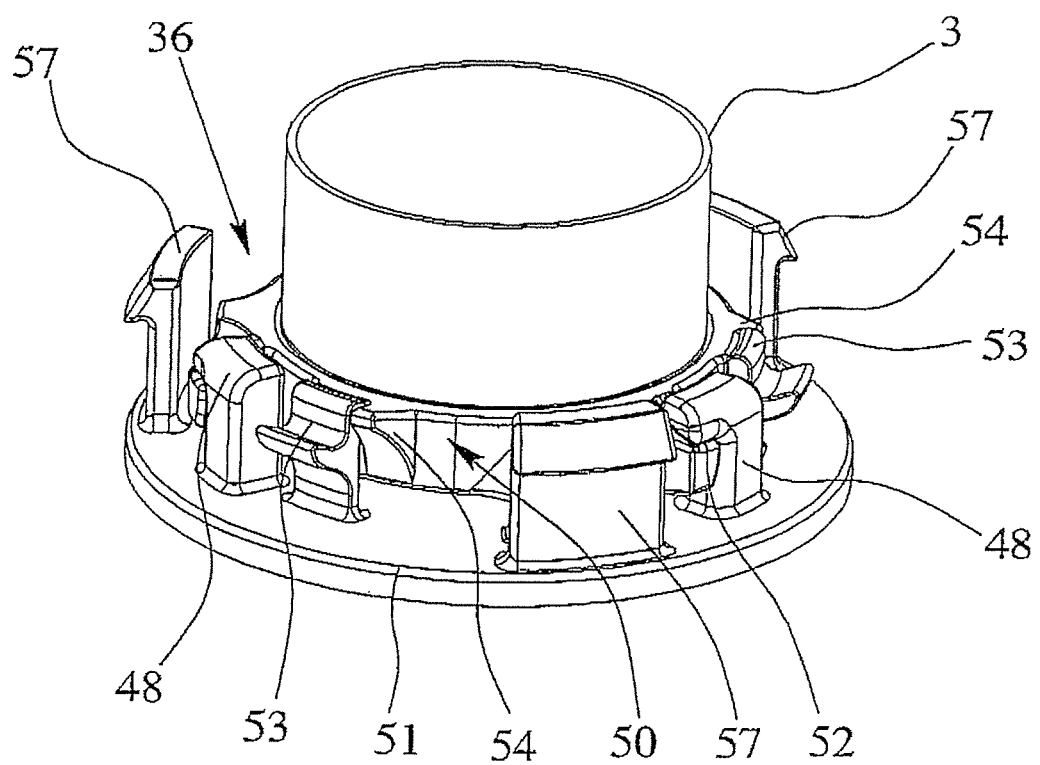
FIG. 26 is a detailed perspective view of a transportation lock for the container in the nebulizer according to the ninth embodiment in the secured state.
Figure 27:
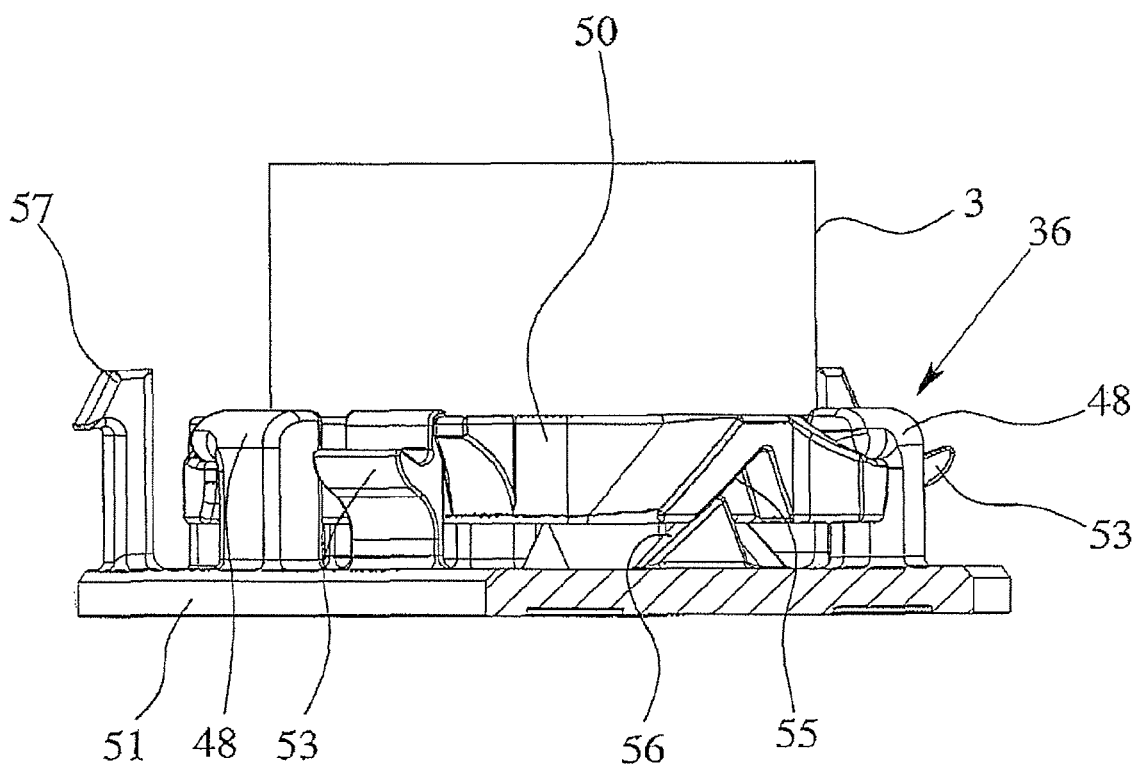
FIG. 27 is a side view, partly in section, of the transportation lock according to FIG. 26 in the secured state.
Figure 28:
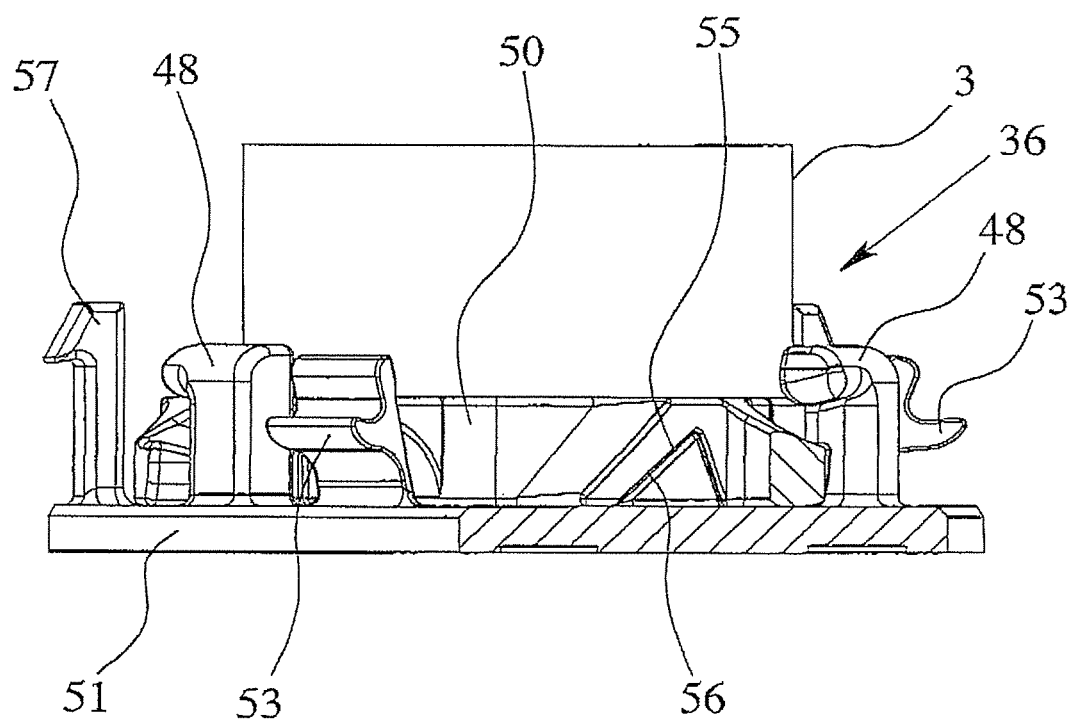
FIG. 28 is a view of the transportation lock, corresponding to FIG. 27, in the open state.
Figure 29:
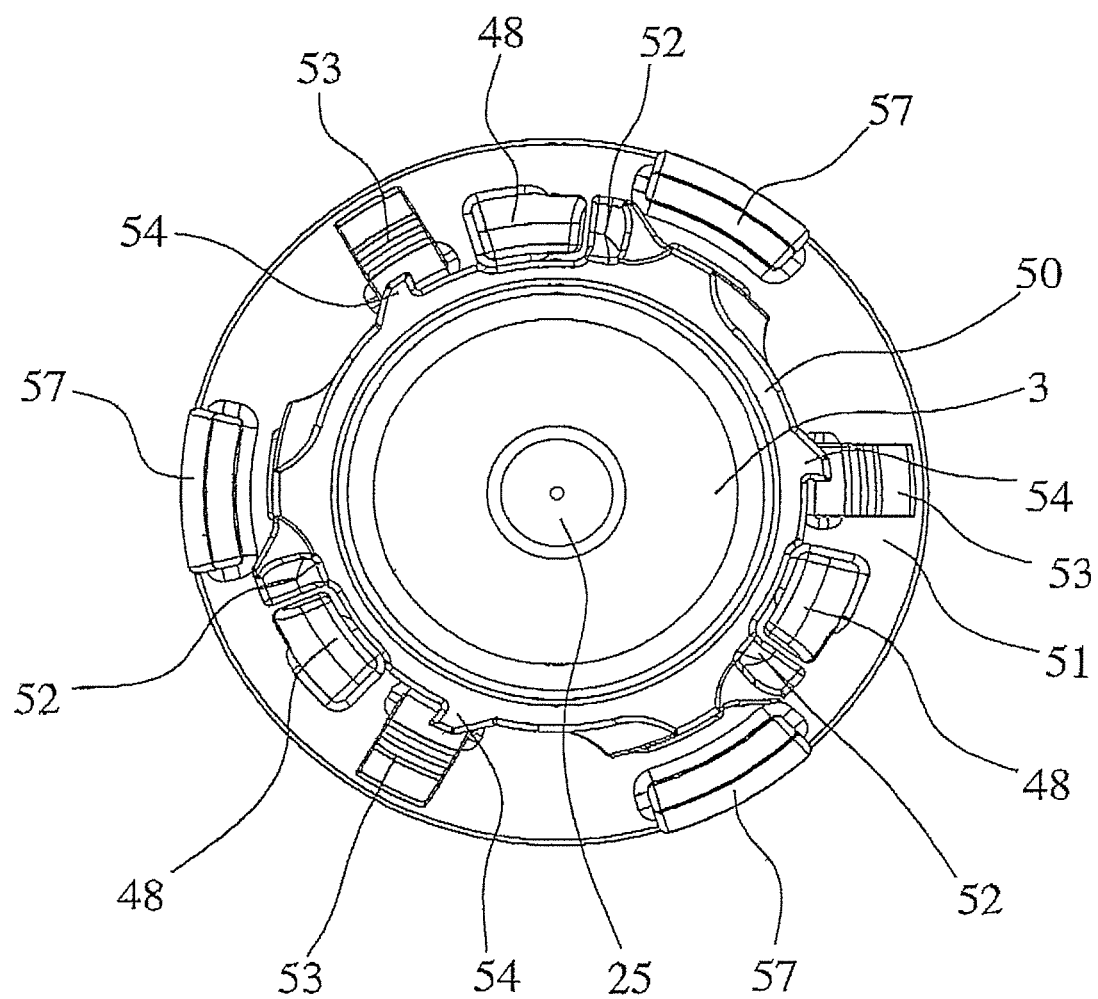
FIG. 29 is a schematic axial view of the transportation lock in the open state.
Figure 30:
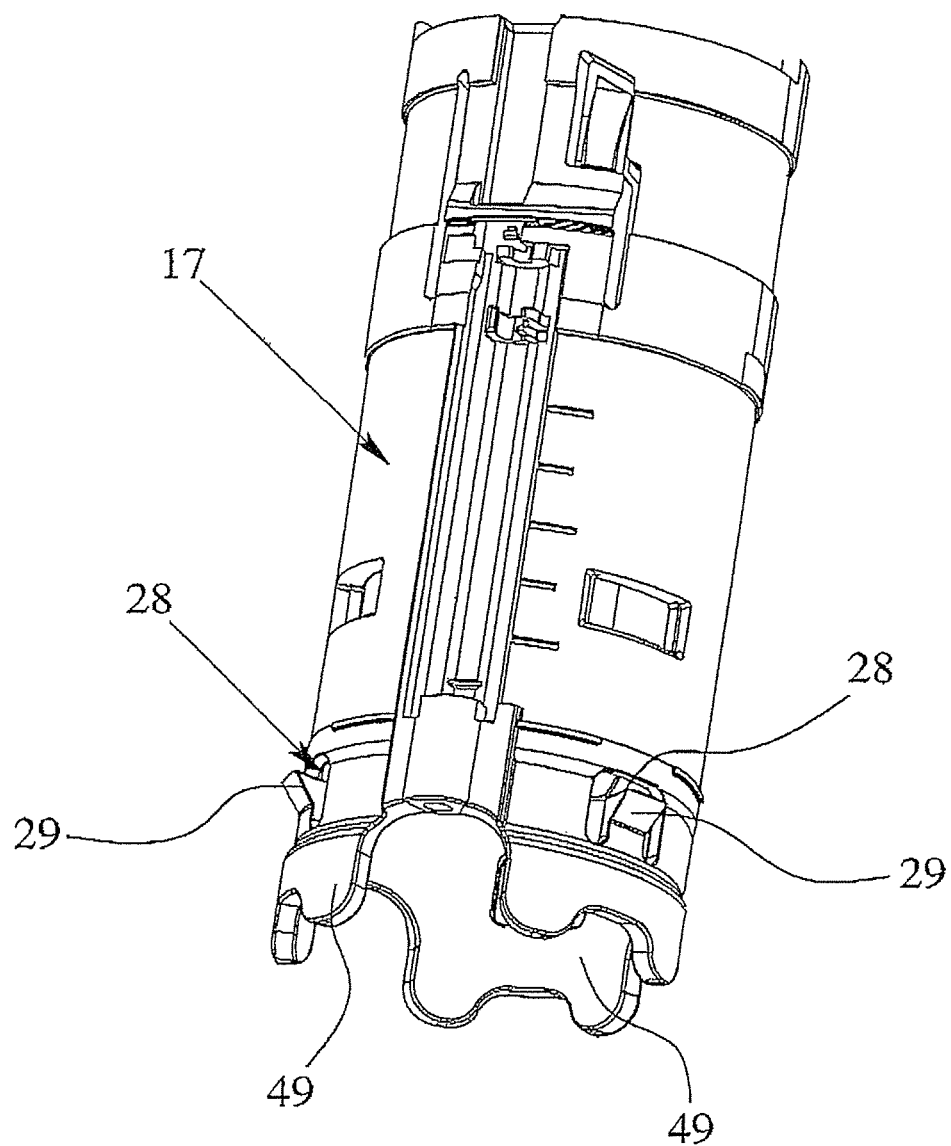
FIG. 30 is a perspective view of an inner part of the nebulizer according to the ninth embodiment.
Figure 31:
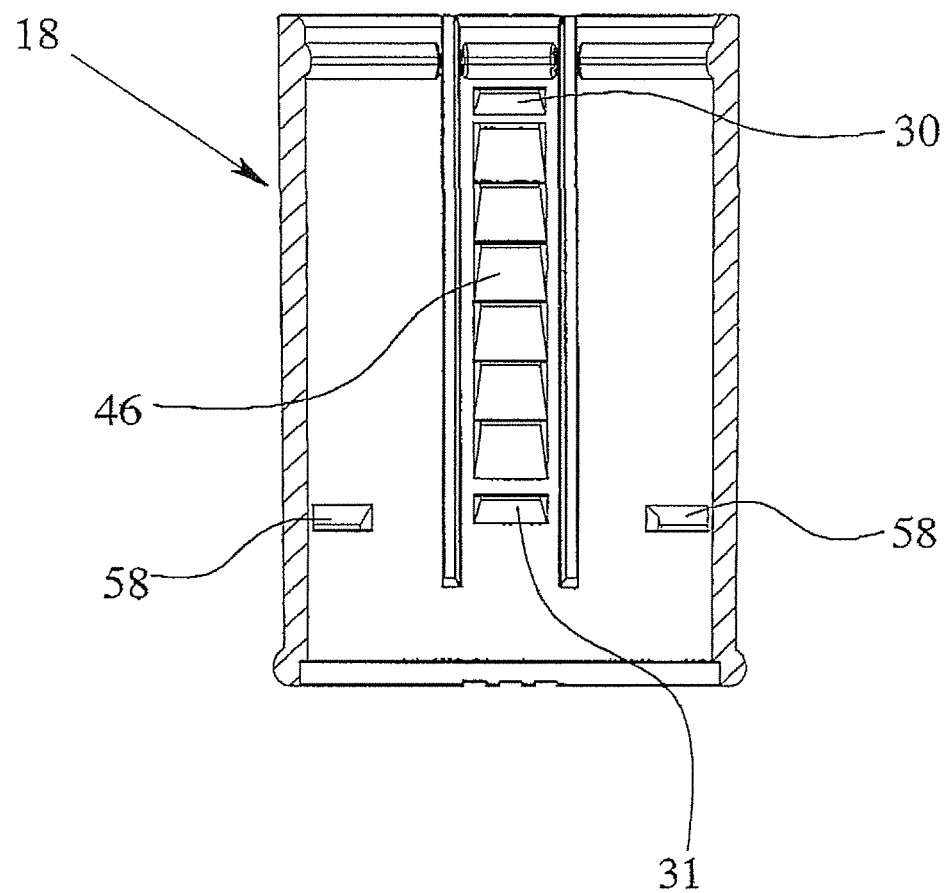
FIG. 31 is a schematic view of a housing part of the nebulizer according to the ninth embodiment.

FIGS. 23 to 31 show a ninth embodiment of the proposed nebulizer 1. FIG. 23 shows the nebulizer 1 in the delivered state. FIG. 24 shows the nebulizer 1 in the activated, but not yet tensioned state. FIG. 25 shows the nebulizer 1 in the activated and tensioned state. FIG. 26 shows, in a detailed perspective view, the transportation lock 36 with a securing element mounted on the container 3, such as a cartridge element 50 and a base element 51 formed or mounted on the housing part 18. FIG. 27 shows in side view the cartridge element 50 in the position where it is axially raised from the base element 51, which is shown partly in section, for clarification. FIG. 28 is a view corresponding to FIG. 27 with the cartridge element 50 in the lowered state. FIG. 29 is a schematic axial view of the transportation lock 36 in the opened state. FIG. 30 shows the inner part 17 of the nebulizer 1 in a perspective view. FIG. 31 shows the housing part 18 in a schematic perspective view.

The ninth embodiment is basically similar to the eighth embodiment in construction and design. The description that follows will mention only the essential differences. The remarks made regarding the eighth embodiment and the other embodiments also supplement one another, in particular.

In the ninth embodiment, the housing part 18 has not been fully pushed on, in the delivered state. The transportation lock 36 fixes the container 3 to the base of the housing part 18 in the delivered state.

In the ninth embodiment, the axial movement is preferably converted on activation into a rotary movement, in order to open the transportation lock 36 or axially free the container 3. In particular, the freeing or release is effected over a diagonal plane. The uncoupling of the movements of axial pushing on and release of the transportation lock 36 by a rotary movement allows optimum axial fixing of the container 3 in the secured state and relatively easy opening of the transportation lock 36 in order to release the container 3 axially. This is explained below with reference to the embodiment shown.

The cartridge element 50 is connected for rotation with the container 3, particularly formed, stuck or injection molded thereon, and encloses the rim or edge of the radially widened container base 21. In the delivered state, as shown in FIGS. 23, 26 & 27, the cartridge element 50 with the container 3 is axially and non-rotatably secured to the base element 51, more specifically at an axial spacing from the base element 51, so that the piercing element 22 on the base element 51 does not open or pierce the base of the container 3.

Rigid gripper arms 48 are mounted, particularly formed, on the base element 51, these arms 48 engaging over radial projections 52 of the cartridge elements 50 in the rotational position specified and thereby securing the cartridge element 50 against moving axially away from the base element 51. Locking arms 53 on the base element 51 block radial stops 54 of the cartridge element 50 and thereby prevent rotation of the cartridge element 50 (in the clockwise direction, in the embodiment shown). Rotation in the opposite direction is blocked by a suitable design of the gripper arms 48 and/or co-operation with sliding inclines 55 on the cartridge element 50 and ramps 56 on the base element 51.

The sliding inclines 55 and ramps 56 extend circumferentially and are inclined in the circumferential direction and matched to one another such that the cartridge element 50 in the (blocked) rotational position specified is held at an axial spacing or raised from the base element 51 in the delivered state, as can be seen from FIG. 27 in particular.

In order to activate the nebulizer 1 and open the container 3 the housing part 18 is fully pushed on in the axial direction. The inner part 17 comprises axial arms or projections 49 shown in FIG. 30, which in the activated state, or when the housing part 18 is fully pushed on, pivot the blocking arms 53 and thereby open the transportation lock 36 or at least undo or unlatch it. The blocking arms 53 or the sections of the blocking arms 53 blocking the radial abutments 54 are swung radially outwards and thereby allow the cartridge element 50 to be rotated relative to the base element 51.

FIGS. 24, 25, 28, & 29 show the cartridge element 51 already rotated clockwise. The rotation is carried out by the sliding of the sliding inclines 55 over the ramps 56, particularly during the tensioning of the pressure generator 5 or the pressing down of the container 3 by the holder 6. During this sliding movement, the cartridge element 50 is moved axially with respect to the base element 51 and the base of the container 3 is pierced by the piercing element 22 on the base element 51. Moreover, the rotation axially frees the cartridge element 50 with the container 3, as the radial projections 52 are moved out underneath the gripper arms 48 and thereby freed axially. The rotation of the cartridge element 50 for optionally piercing the container 3 and axially releasing it is preferably about 5 to 10°.

Naturally, the transportation lock 36 may also be of a different construction, but with a comparable function; in particular, it should allow for the opening or at least undoing or releasing of the transportation lock 36 by rotating the cartridge element 50 relative to the base element 51 in the counterclockwise direction.

The principle described above or the specific construction of the transportation lock 36 according to the ninth embodiment may, if necessary, also be implemented in the other embodiments, particularly in the eighth embodiment.

The base element 51 preferably has retaining arms 57, which engage in corresponding notches 58 on the housing part 18 for attachment to said housing part 18. In particular, during assembly, the base element 51 is clipped into the housing part 18, preferably together with the container 3 and the cartridge element 50. This allows easy assembly. However, the base element 51 may also be attached to the housing part 18 in some other way and/or be formed thereby.

In the embodiment shown, the inner part 17 comprises several, particularly three, latching arms 28 distributed over the circumference. The housing part 18 shown by way of example in FIG. 31, however, preferably has only one latching member 46 on the inside, into which accordingly only one associated latching arm 28 engages with its latching lug 29. The function of this engagement has already been discussed with reference to the sixth and eighth embodiments, in particular, and there is therefore no need to go into it again at this point.

The other latching arms 28 engage in latching recesses 30, 31 on the housing part 18, the recesses 30 corresponding to the axial position in the delivered state and the recesses 31 corresponding to the axially fully inserted position of the housing part 18. This results in a particularly durable securing of the housing part 18 in both positions, to rule out the possibility of the housing part 18 being detached from the nebulizer 1 by a user or of unauthorized partial axial removal of the housing part 18 from the fully pushed-on position.

In the ninth embodiment, the housing part 18 is preferably mounted in non-rotatable manner on the nebulizer 1 or inner part 17 as in the other embodiments.

In the ninth embodiment, the activation is preferably carried out with an untensioned nebulizer 1 or pressure generator 5. Accordingly, after activation by axial insertion of the housing part 18, a first tensioning is still required in order to bring the holder 6 into engagement with the container 3, as indicated in FIG. 25.

However, the nebulizer 1 or pressure generator 5 may also already be tensioned in the delivered state. This is the case particularly in the first, second, third, fifth, sixth and seventh embodiments.

According to a particularly preferred alternative embodiment, the cartridge element 50 and the container 3 are inseparably attached to one another. Preferably, the cartridge element 50 serves to code the container 3 or the fluid 2 or drug contained therein. The coding may vary, for example, depending on the particular active substance and/or the dosage. The coding by the cartridge element 50 ensures that the container 3 with the cartridge element 50 can only be used in conjunction with a specific nebulizer 1, particularly only with a specific or matching housing part 18 or base element 51. This is a way of ensuring that only the correct container 3 or the correct fluid 2 is used with the relevant nebulizer 1.

The coding is, in particular, a corresponding adaptation or complementary structure of projections, recesses, undercuts, arrangement and number of arms or the like, to ensure that the container 3 in question with the cartridge element 50 can only be inserted in the nebulizer 1 if the coding matches, i.e., if the parts fit.

With regard to the cartridge element 50, it should generally also be pointed out in connection with the ninth embodiment that it does not necessarily have to be of continuous peripheral construction. Rather, it may, if necessary, also extend only over part of the circumference of the container 3, especially along the container base 21. However, the container 3, instead of the cartridge element 50, may also be provided with, or may form, some other securing element or the like (not shown) which cooperates in particular only mechanically with the base element 51, for example, by a correspondingly suitable design of the container rim in the region of the container base 21 or the like.

Figure 32:
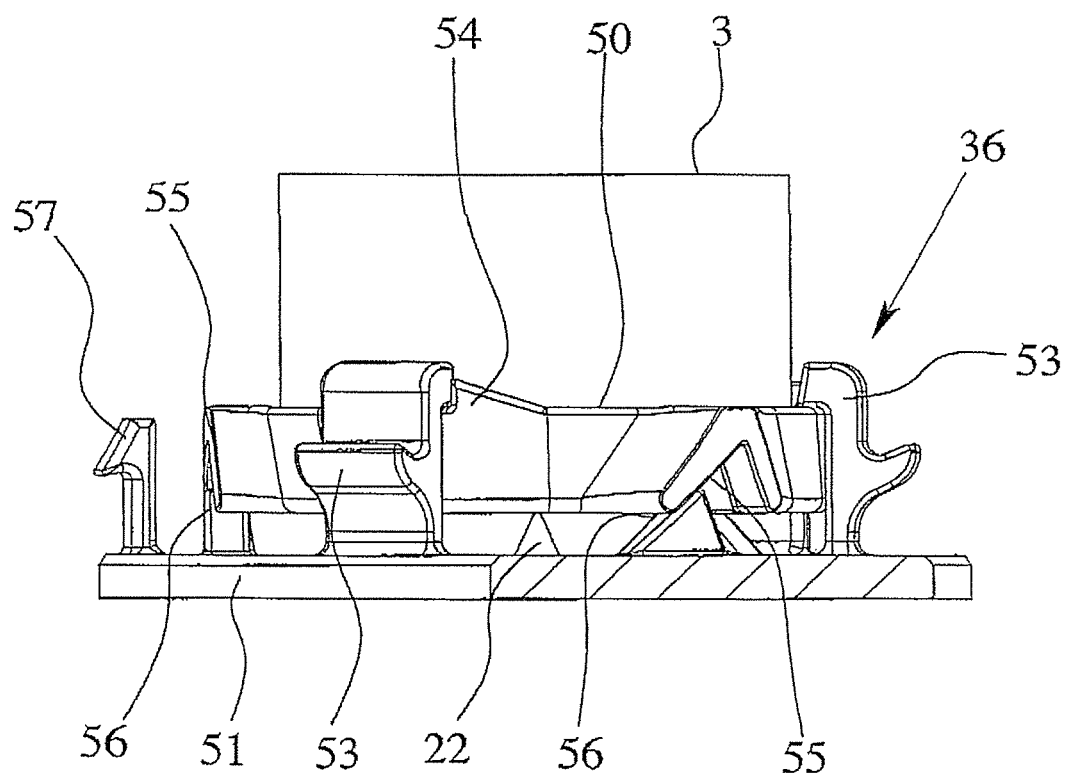
FIG. 32 is a side view, partly in section, of a transportation lock for a nebulizer according to a tenth embodiment in the secured state.
Figure 33:
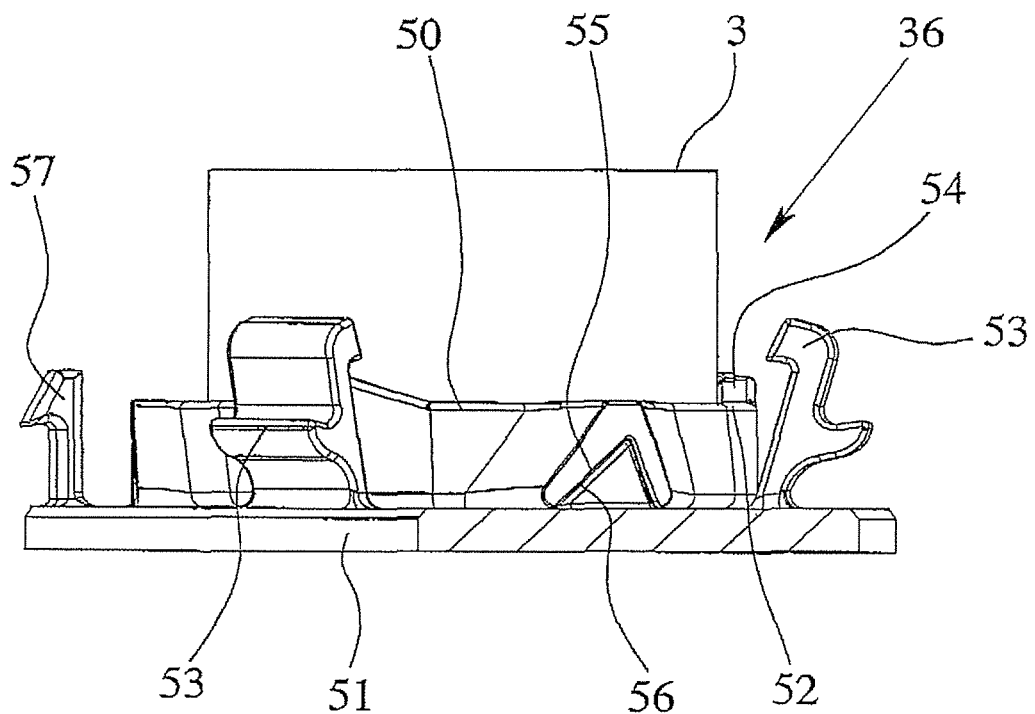
FIG. 33 is a view of the transportation lock corresponding to FIG. 32, in the opened state.

A tenth embodiment of the nebulizer 1 or transportation lock 36 will now be explained in more detail with reference to FIGS. 32 and 33. FIG. 32 corresponds to the view in FIG. 27. FIG. 33 corresponds to the view in FIG. 28.

The tenth embodiment differs from the ninth embodiment essentially only in its somewhat simpler construction of the transportation lock 36. Compared with the ninth embodiment, the gripper arms 48 are missing from the tenth embodiment. Instead, the blocking arms 53, in the secured state, additionally, serve to fix or secure the cartridge element 50 axially to the base element 51 or housing part 18. In particular, the blocking arms 53 engage with corresponding, preferably angled sections, over the cartridge element 50 or suitable projections of the cartridge element 50, such as the radial projections 52, to secure the cartridge element 50 against being lifted radially out of the position shown in FIG. 32.

FIG. 33 shows the already unsecured state or the already opened transportation device 36. The blocking arms 53 are deflected, particularly pivoted radially outwards, in order to release the cartridge element 50 and hence the container 3 axially. Moreover, in the position shown in FIG. 33, the cartridge element 50 together with the container 3 has already been placed on the base element 51; this is done by the action of the holder 6 during the tensioning of the nebulizer 1 with the transportation lock 36 open. The container 3 has thus been pierced in the base in this state.

The other explanations and aspects relating to the ninth embodiment also fundamentally apply accordingly or at least in supplementary fashion to the tenth embodiment as well.

FIGS. 34 to 40 show an eleventh embodiment of the proposed nebulizer 1.

Figure 34:
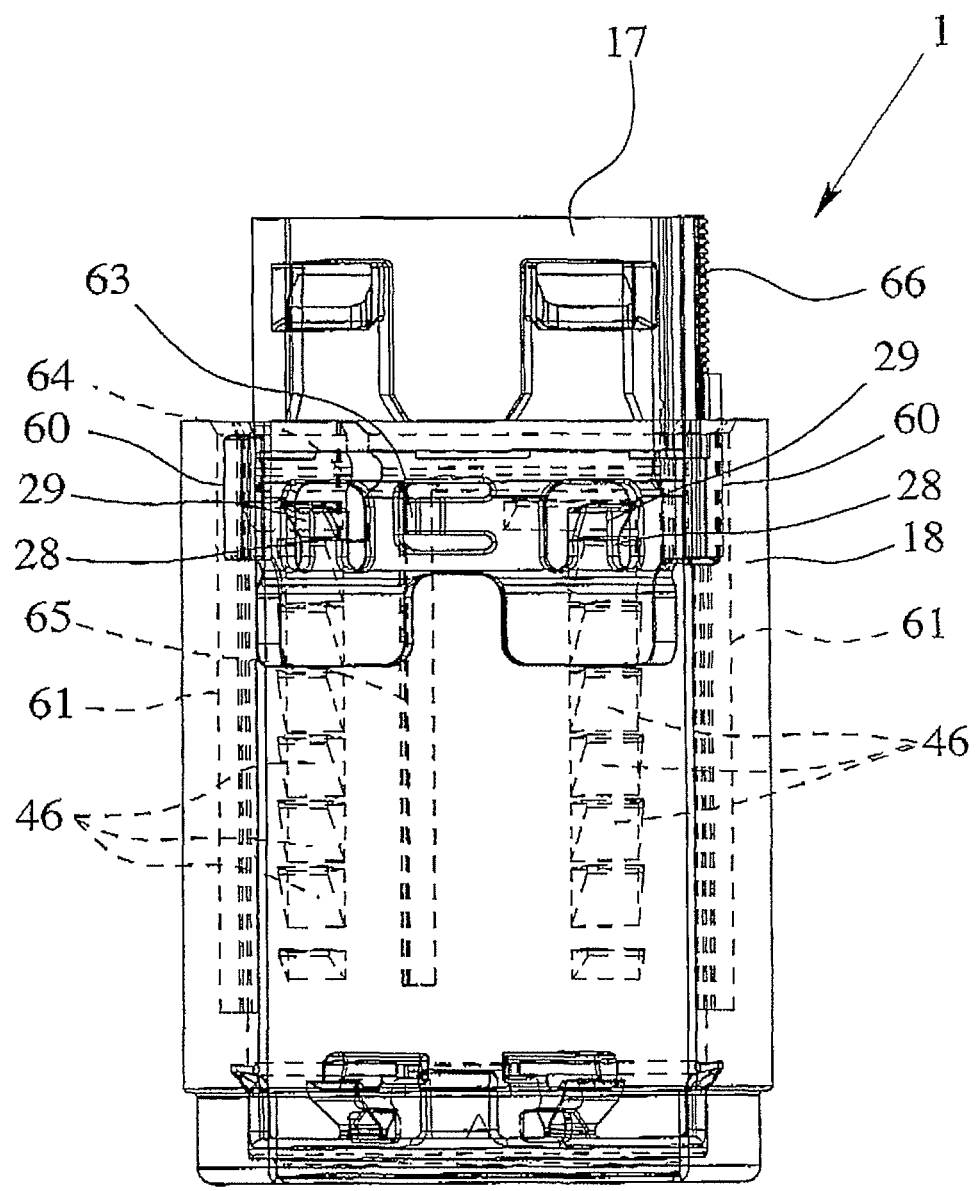
FIG. 34 is a schematic section through a lower part of a proposed nebulizer according to an eleventh embodiment in an intermediate state.

FIG. 34 shows the nebulizer 1—or, more precisely, a lower part of the nebulizer 1—in a schematic, partially transparent side view in an intermediate state. A container 3 is not shown therein. The housing part 18 is in the lower or first position, in which the housing part 18 is held at an axial spacing from the inner part 17 by the upper housing part 16, so that a container 3 located in the housing part 18 is still spaced from the conveying element or conveying tube 9, i.e., has not yet been opened or pierced.

Figure 35:
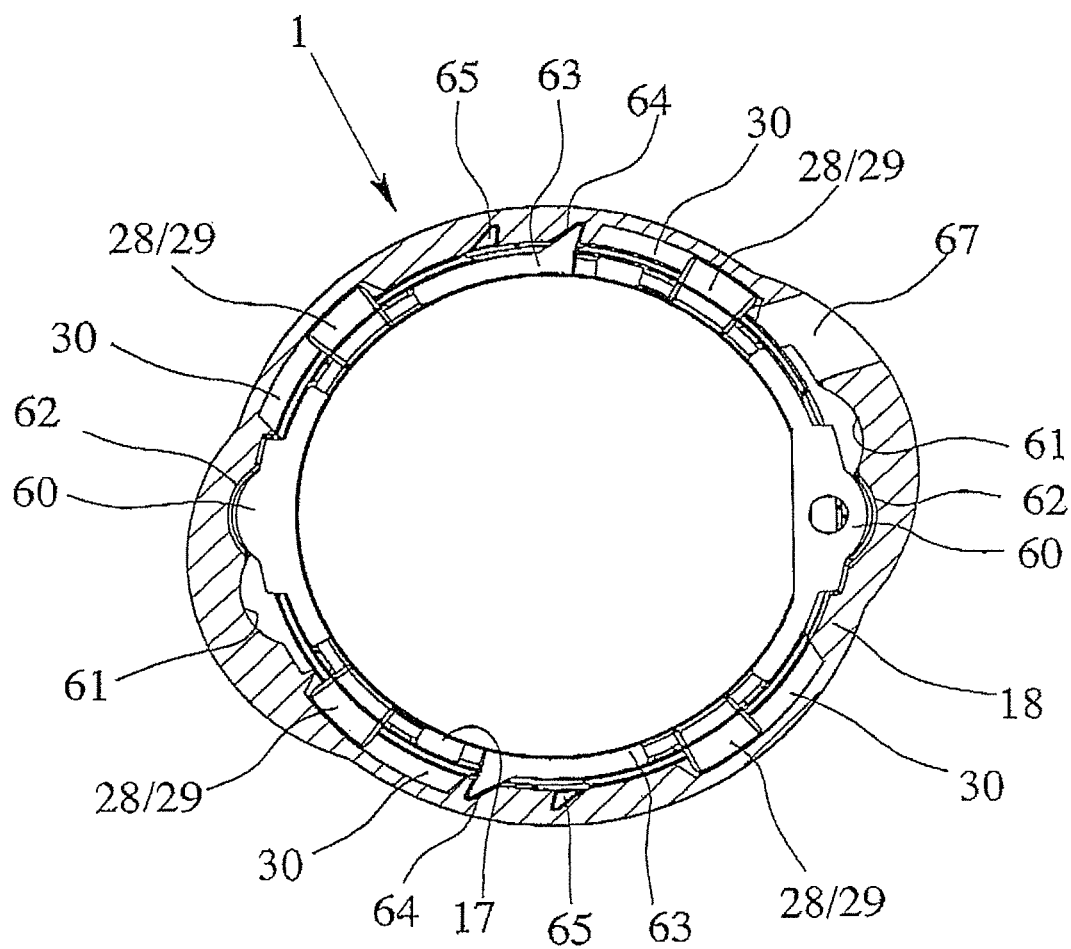
FIG. 35 is a schematic axial section through the nebulizer according to FIG. 34 in the area of overlap of a housing part with an inner part in the delivered state.
Figure 36:
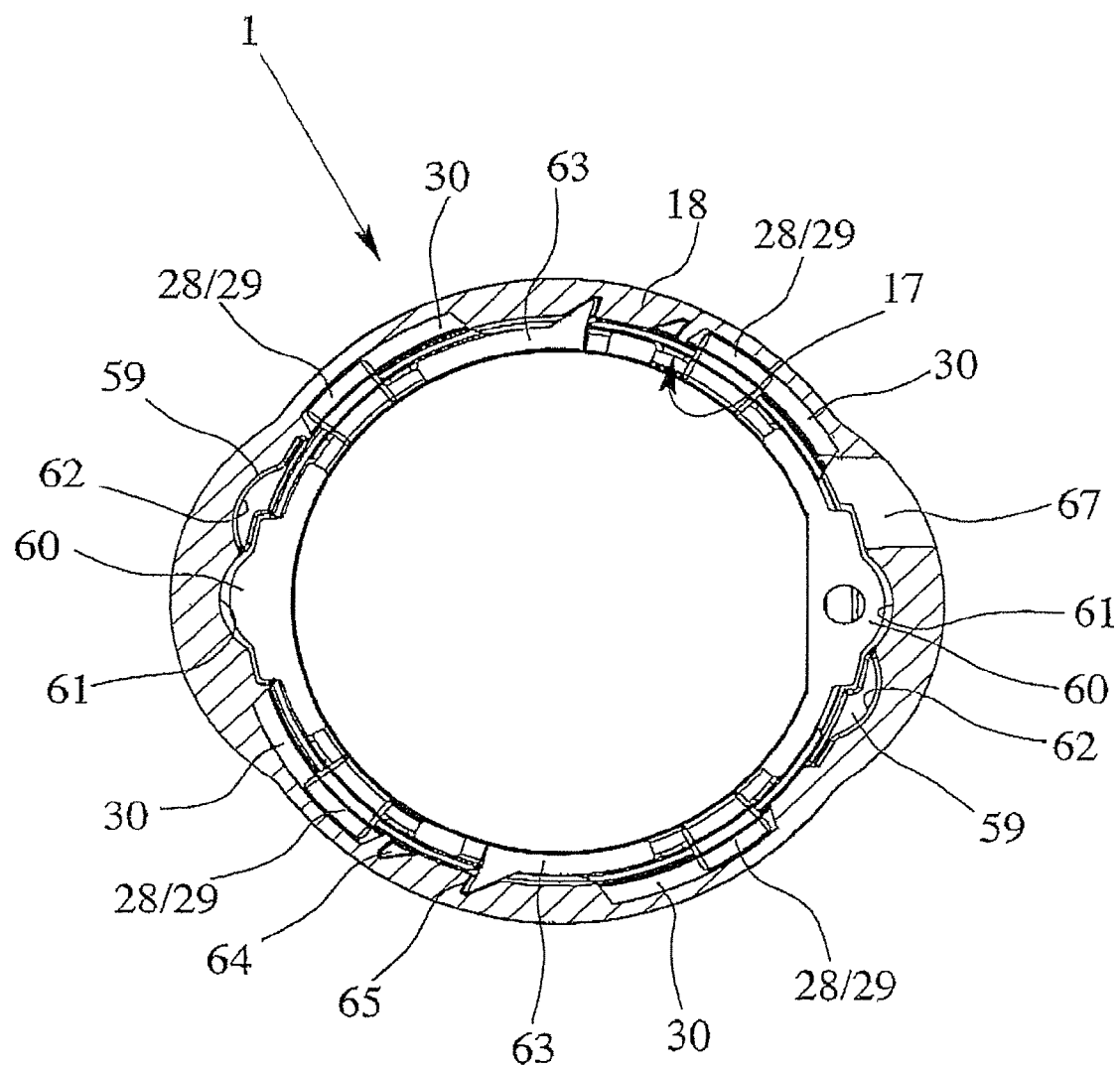
FIG. 36 is a schematic axial section through the nebulizer according to FIG. 34, corresponding to FIG. 35, in the intermediate state.
Figure 37:
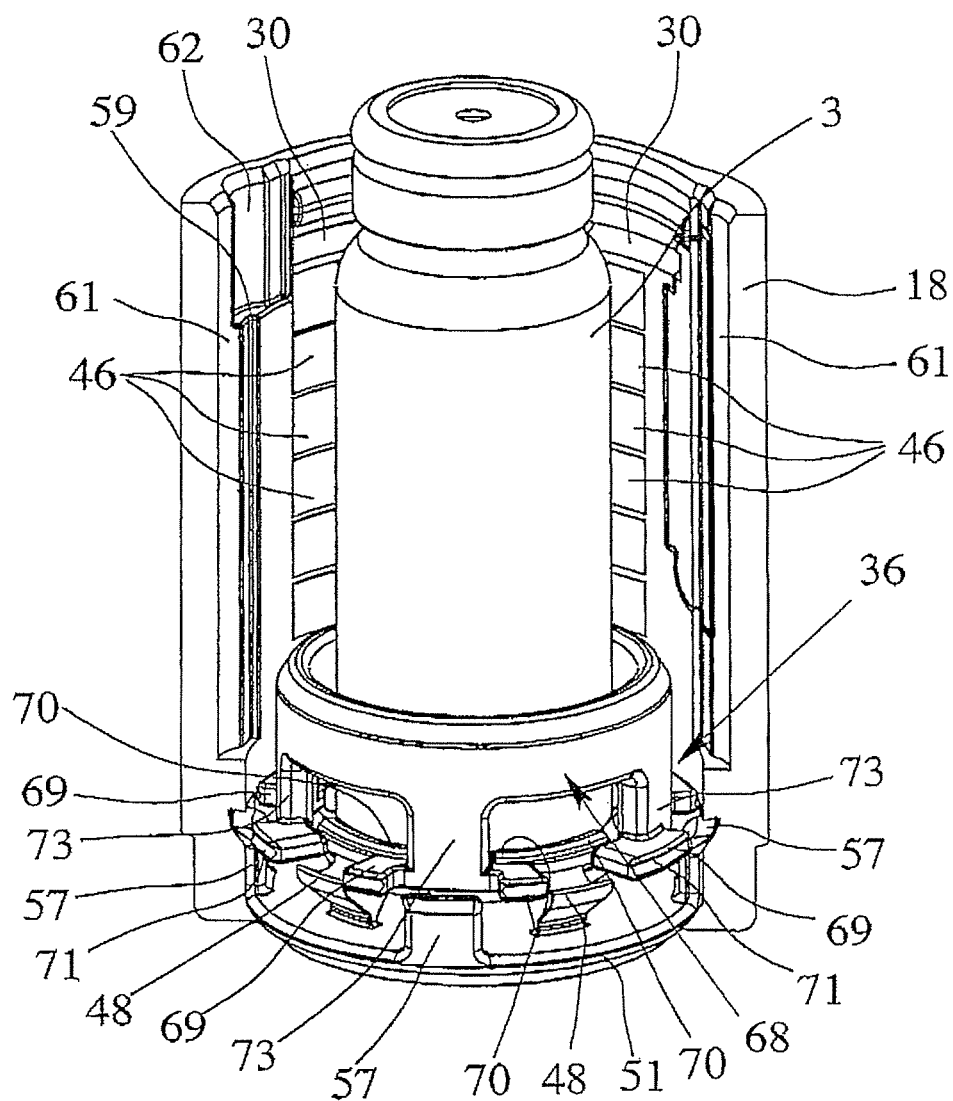
FIG. 37 is a perspective side view, partly in section, of the housing part with a container and a transportation lock for the nebulizer according to FIG. 34.
Figure 38:
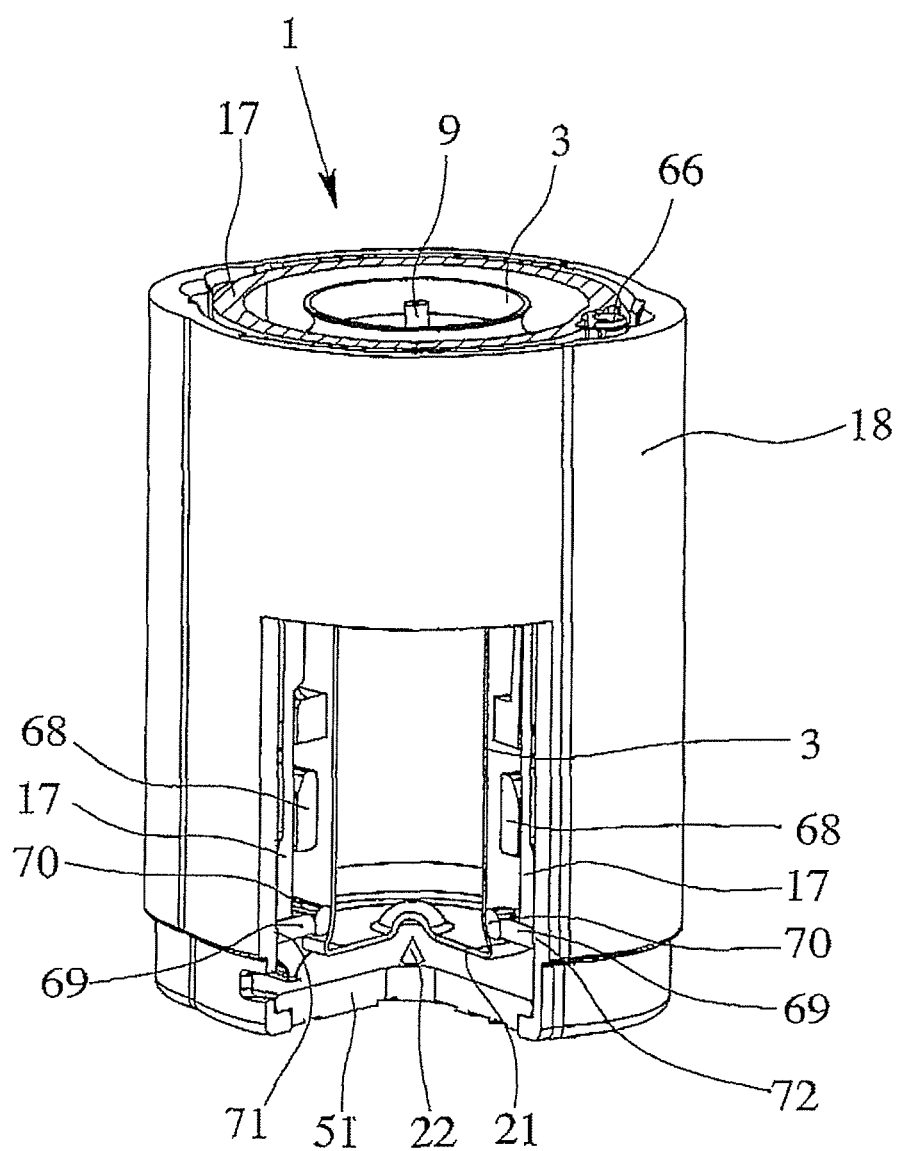
Figure 39:
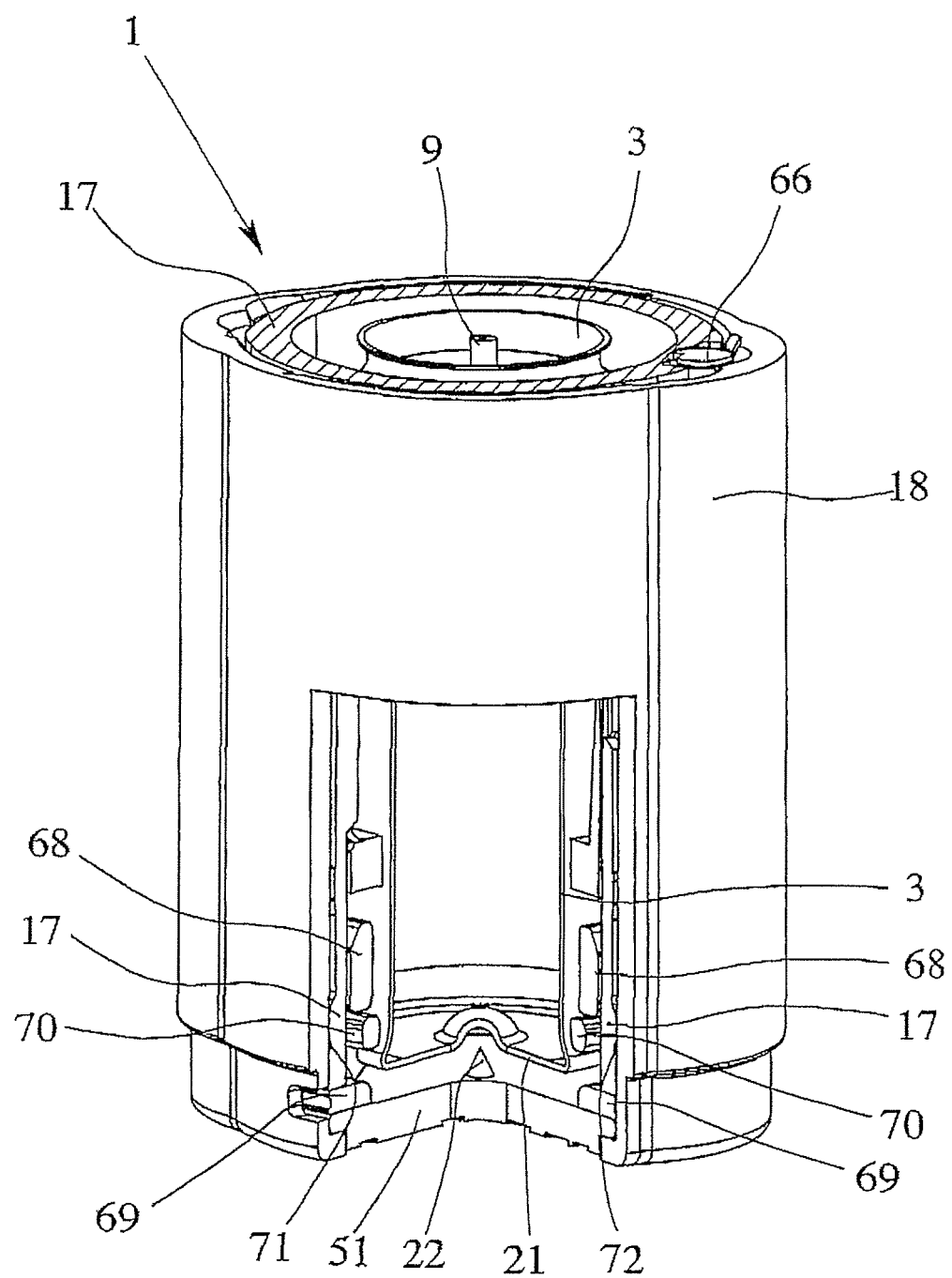
Figure 40:
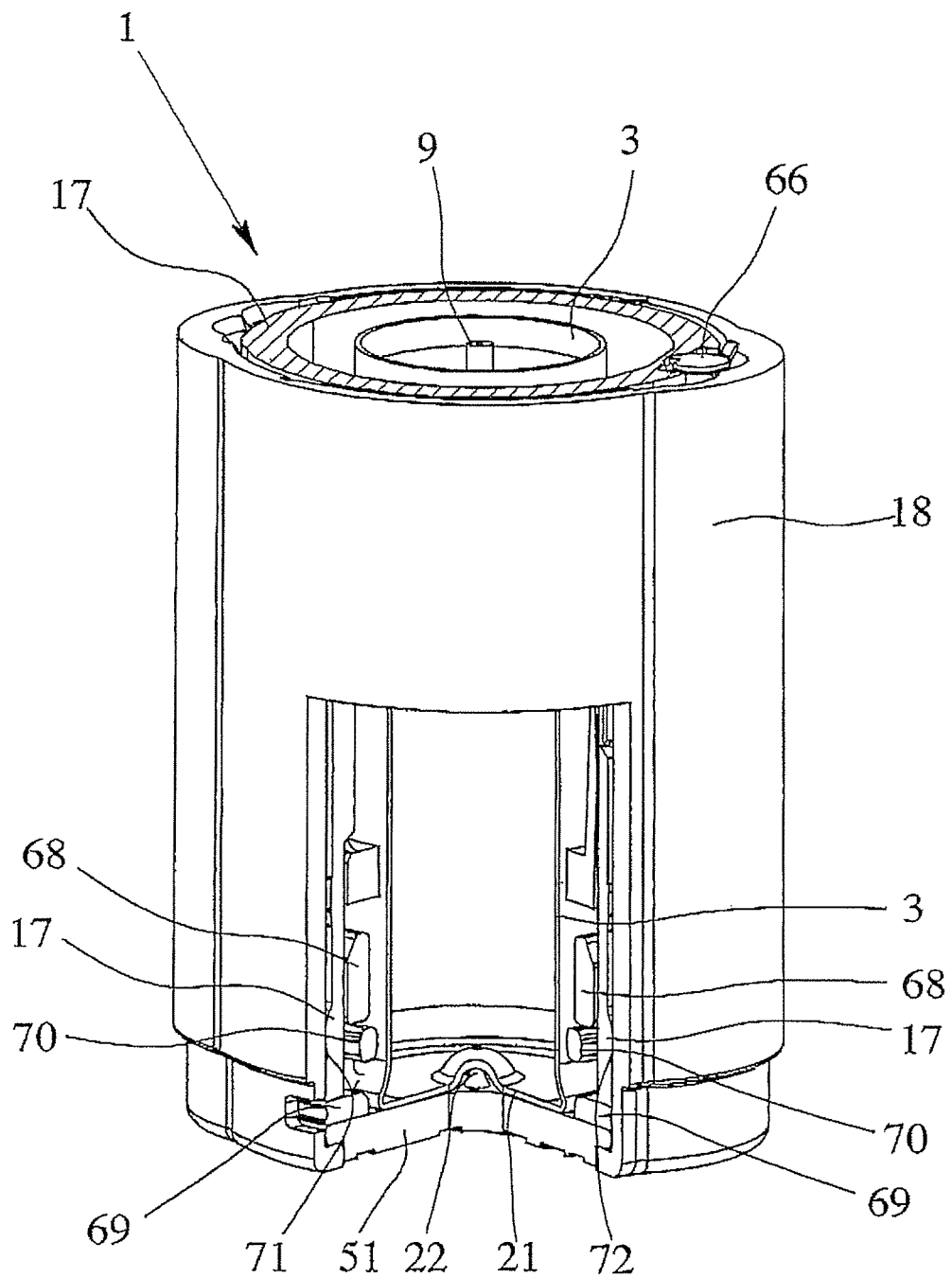
FIG. 40 is a perspective side side view, partly in section, of the housing part of the nebulizer according to FIG. 34 with the container opened or pierced at the base.

FIG. 35 shows in axial section the relative rotary position of the housing part 18 from the inner part 17 in the delivered state. FIG. 36 shows the rotary position of the housing part 18 relative to the inner part 17 in the intermediate state shown in FIG. 34. Here, the housing part 18 is rotated relative to the inner part 17 or to the delivered state. FIG. 37 shows, in a partially sectional side view, the housing part 18 without the inner part 17, but with the container 3 and a transportation lock 36 holding the container 3 in the housing part 18. FIGS. 38 to 40 show partially sectional side views of the housing part 18 in various states.

The eleventh embodiment is basically very similar to the seventh, eighth, ninth and/or tenth embodiments, and therefore reference is made to the remarks and explanations and illustrations provided in relation thereto, which apply accordingly or in a supplementary capacity. Only essential differences or new aspects of the eleventh embodiment will be described in more detail below.

In the delivery position shown in FIG. 35, the housing part 18 is prevented, preferably by interlocking engagement, from being pushed axially (further) onto the inner part 17 or from moving closer to the upper housing part 16. Only after rotation of the housing part 18 relative to the inner part 17—preferably through about 10° to 20°—into the intermediate position shown in FIGS. 34 & 36 can the (further) axial insertion or the activation of the nebulizer 1 take place, and only then is the container 3 opened and fluidically connected, as already explained in the other embodiments.

The above-mentioned rotary movement of the housing part 18 relative to the inner part 17 from the delivery position into the intermediate position is essential to enable the housing part 18 to be axially pushed on afterwards or the nebulizer 1 to be activated. The axial blocking of the housing part 18 in the delivery position thus constitutes a protection against accidental activation of the nebulizer 1. For example, this prevents the nebulizer 1 from being accidentally activated when dropped.

During assembly, the housing part 18 together with the container 3 located therein, held by the transportation lock 36, is initially pushed onto the inner part 17 or the lower part 17b of the inner part 17 only until the housing part 18 is inseparably attached, particularly latched and secured to the inner part 17. Particularly preferably in the delivered state latching arms 28 with latching lugs 29 engage in first latching recesses 30, so that the housing part 18 can no longer be detached or pulled away from the inner part 17. In this delivered state, the housing part 18 is then at least initially protected by interlocking engagement from any further axial pushing.

The locking to prevent any further axial pushing in the delivered state is preferably achieved in the embodiment shown by provision on the housing part 18 of at least one axial abutment 59, in particular at least two axial abutments 59 on opposite sides, which butt up against at least one preferably radial projection 60 on the inner part 17 in the delivered state. The abutments 59 are most clearly shown in the end view according to FIG. 36. Here, the housing part 13 has already been rotated into the intermediate position, so that the projections 60 no longer axially overlap the abutments 59, but engage in adjacent axial recesses 61.

The rotation of the housing part 18 relative to the inner part 17 from the delivery position into the intermediate position is possible, inter alia, because the latching recesses 30 have a corresponding peripheral extent, so that the latching lugs 29 are able to slide or move along the circumference in the inner wall of the housing part 18, more precisely in the intermediate position shown in FIG. 34.

Locking against further axial pushing of the housing part 18 in the delivered state can also be achieved by other constructional means.

On rotating the housing part 18 from the delivery position into the intermediate position, a certain resistance preferably has to be overcome. The rotary action may be made stiff for this purpose. In the embodiment shown, the housing part 18 moves into the delivery position and the intermediate position in a virtually latching manner (in the delivery position the radial projections 59 engage in radial recesses 62 and in the intermediate position they engage in the adjacent axial recesses 61 in the housing part 18), so that a certain latching resistance has to be overcome when moving from the delivery position into the intermediate position, while the housing part 18 and/or inner part 17 are preferably radially elastically deformed accordingly or cause corresponding portions to yield resiliently.

Preferably, a locking device is also provided, so that the housing part 18 cannot be rotated back out of the intermediate position into the delivery position. In the embodiment shown, on the inner part 17 is provided at least one preferably radially acting locking latch 63, which initially engages in the delivery position in a first axially extending latching notch 64 in the housing part 18, and in the intermediate position, in a second axially extending latching notch 65. During the transition from the delivery position into the intermediate position—i.e., from the first latching notch 64 into the second latching notch 65—the locking latch 63 can yield radially inwards. In the embodiment shown, two locking latches 63 are provided on opposite sides together with associated latching notches 64 & 65. Rotation back from the intermediate position into the delivery position can also be prevented by other constructional means.

In the eleventh embodiment, the activation of the nebulizer 1 requires a combination of a rotary and a translatory movement. This combined movement results in particularly good securing against accidental activation of the nebulizer 1.

Preferably, in the non-activated state, i.e., when the housing part 18 has not been pushed on fully—the nebulizer is locked to prevent tensioning of the pressure generator, i.e., in particular, to prevent rotation of the inner part 17 relative to the upper housing part 16. This is particularly important when the nebulizer 1 is supplied in the delivered state with the pressure generator 5 not under tension. Accordingly, the inhaler 1 has a barrier, so that the inner part 17 can only be rotated relative to the upper housing part 16 when the housing part 18 has been pushed fully on. This rotation barrier which is effective particularly in the delivered state may also be used independently of the eleventh embodiment in the other embodiments in which the nebulizer 1 is delivered in the untensioned state.

The direction of rotation when moving the housing part 18 from the delivery position into the intermediate position preferably extends in the opposite direction to the direction of rotation when tensioning the pressure generator 5 or nebulizer 1 by rotating the housing part 18 in the activated state. However, the rotation from the delivery position into the intermediate position may alternatively also be carried out in the direction of tensioning, in order to tension the nebulizer 1 or pressure generator 5 at the same time, if desired.

In the embodiment shown, one of the radial projections 60 preferably forms a bearing for the counting or monitoring device 23, particularly for a threaded spindle 66 of the device 23, shown in FIG. 34. The spindle 66 is preferably a slider (not shown) for indicating the number of doses which have already been taken or which are still available to take. By rotating the spindle 66, the slider can be moved along the spindle 66. Preferably, a window 67 (c.f. FIGS. 35 & 36) is formed in the housing part 18 so that the axial position of the slider can be seen, even if the housing part 18 is not otherwise transparent in construction.

The eleventh embodiment has a transportation lock 36 which is rather different in construction from those in the previous embodiments. The function of the transportation lock 36, however, corresponds to the remarks made previously, and therefore only the essential differences in the transportation lock 36 will be discussed hereinafter.

FIG. 37 illustrates the preferred structure of the transportation lock 36. A base element 51 is inserted in the housing part 18 and held by retaining arms 57. The transportation lock 36 or the base element 51 comprises gripper arms 48 which fix the container 3 in the transportation state shown. In particular, the gripper arms 48 engage radially and/or axially on the container 3 or the transition to its base 21 in this state, in order to secure the container 3 by frictional or, more particularly, interlocking engagement. The gripper arms 48 are distributed around the circumference of the container 3.

The transportation lock 36 also has a preferably annular securing element 68 which is provided with, in particular, radially extending locking elements 69 which prevent the gripper arms 48 from springing radially outwards in the secured state or transportation state shown. In particular, the locking elements 69 for this purpose engage on peripheral or lateral (hammer-like) projections 70 on the gripper arms 48 radially from the outside.

Preferably, the locking elements 69 are supported radially on the outside on the inner wall of the housing part 18 (this prevent radial deflection and correspondingly ensures blocking or locking of the gripper arms 48), by interlocking engagement, in the transporting position which holds the container 3 by interlocking engagement; and are preferably axially held on the radial exterior by a peripheral groove 71 and an associated peripheral bead 72 on the housing part 18, as indicated in FIG. 38, or in some other way. Thus, the securing element 68 is axially fixed or held in the transportation state. However, the securing element 68 may also be axially held directly or in some other way.

The locking elements 69 are preferably connected to the securing element 68 by axial bars 73, so as to form between them spaces which are large enough to enable the gripper arms 48 to yield outwards when the transportation lock 36 is opened and in the axial direction, particularly with the securing element 68 pushed towards the base of the housing part 18, as will be described hereinafter.

FIG. 38 shows the housing part 18 with the inner part 17 already partly inserted, so that axial arms or projections 49 of the inner part 17 are already abutting on the end faces of the locking elements 69. Starting from the intermediate position the container 18 has not yet been pushed fully onto the inner part 17 or nebulizer 1.

FIG. 39 shows the position with the housing part 18 fully pushed on. The inner part 17 has pushed the securing element 68 out of the securing or transportation position shown in FIGS. 37 & 38 axially towards the base of the housing part 18, so that the locking elements 69 no longer secure the gripper arms 48 against axial deflection. During the axial displacement the inner part 17 has overcome or cancelled the interlocking engagement which is preferably provided between the housing part 18 and the locking elements 69.

Moreover, on reaching the position shown in FIG. 39, the inner part 17 has radially deflected the gripper arms 48 by corresponding axial engagement and thereby opened the transportation lock 36. In this position, the container 3 is already held at the head end by the holder 6, even if the container 6 has possibly not yet fully engaged in the holder 6.

During the subsequent tensioning of the nebulizer 1 or pressure generator 5 for the first time, the holder 6 is moved further axially in the direction of the housing part 18, as a result of which the container 3 is latched at its head end to the holder 6, in the desired manner, unless this has already occurred, and the container 3 is moved into its lower axial end position, so that it is opened or pierced at the base by the piercing element 22, as indicated in FIG. 40.

The nebulizer 1 preferably has an indicator device for indicating the activated state or the opened state of the transportation lock 36. In the embodiment shown this is achieved by the fact that the housing part 18 has a lateral inspection window 74 in its base region. A peripheral, preferably differently colored part of the securing element 68, particularly of a locking element 69, is visible through the inspection window 74 only when the transportation lock 36 is open or the inner part 17 is fully engaged.

The transportation lock 36 allows easy assembly, particularly easy insertion of the container 3 into the housing part 18, very secure holding of the container 3 in the transportation position and easy reliable opening by the inner part 17 or the like.

The transportation lock 36 according to the eleventh embodiment can also be used in the other embodiments.

Figure 41:
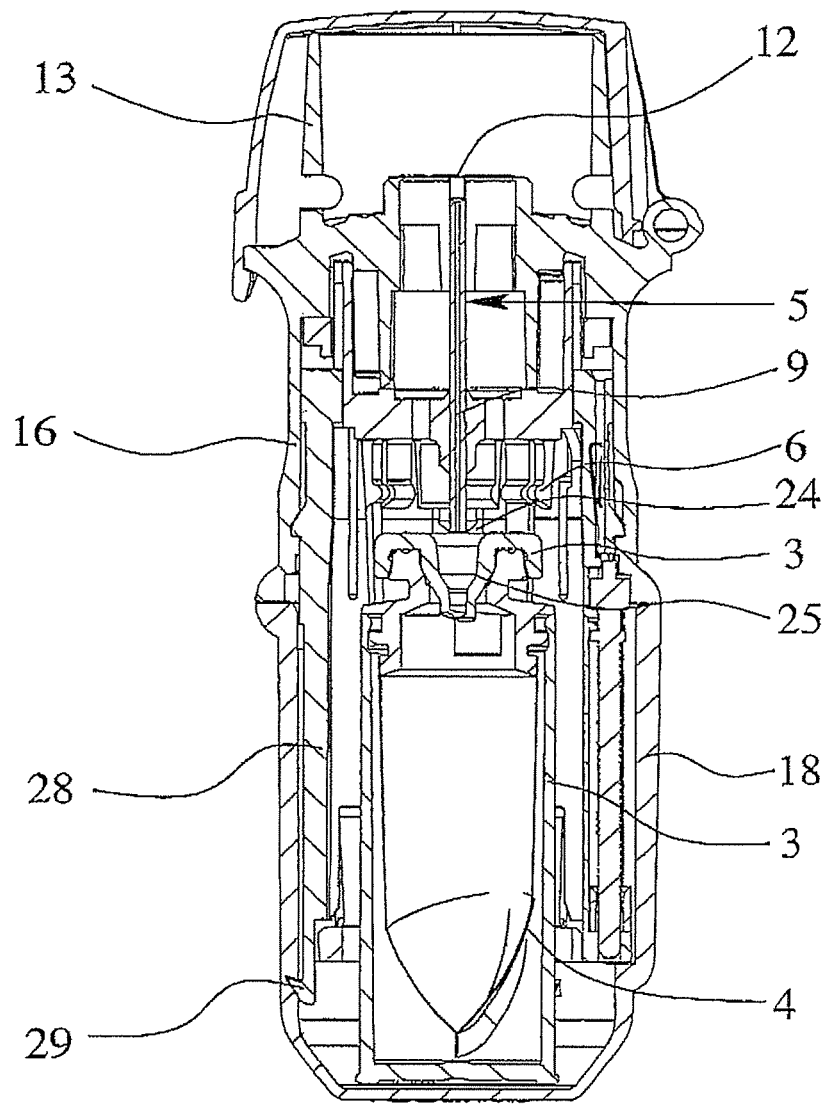
FIG. 41 is a schematic section through a proposed nebulizer according to a twelfth embodiment in the delivered state with a sealed container incorporated therein.
Figure 42:
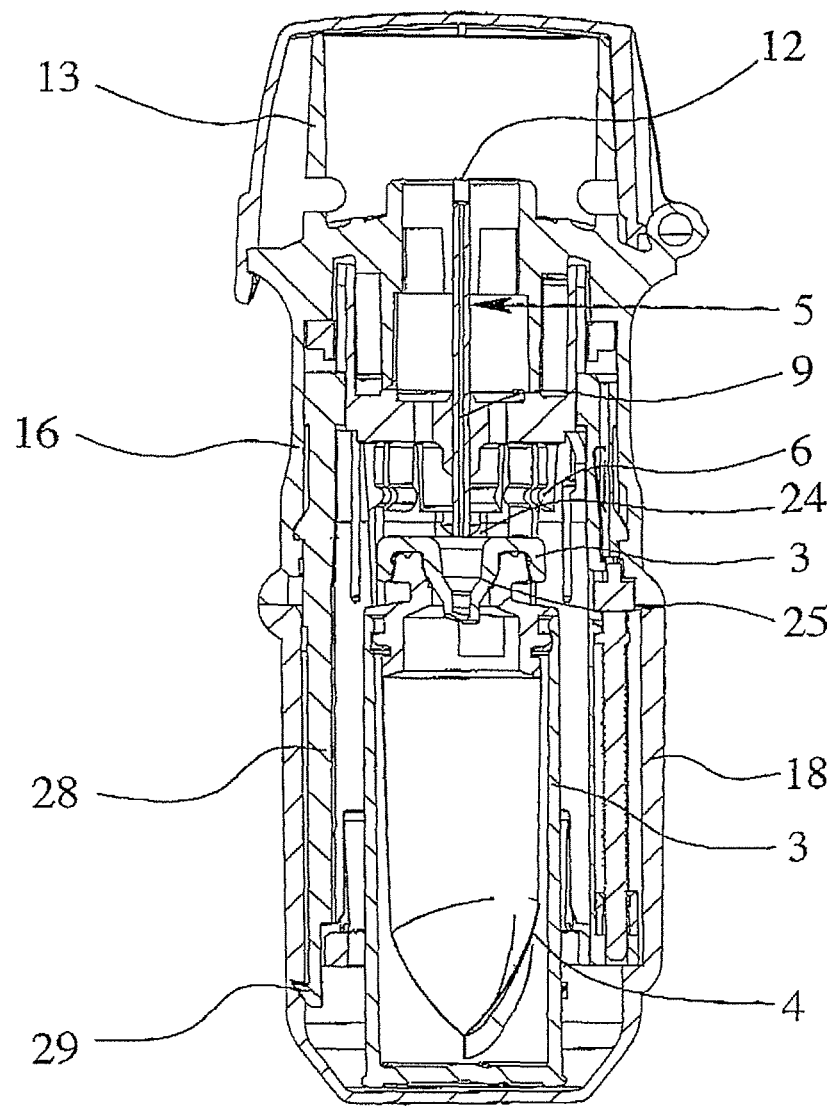
FIG. 42 is a schematic section through the nebulizer according to FIG. 41 in the activated tensioned state or with the container opened.

FIGS. 41 & 42 are schematic sections through a twelfth embodiment of the proposed nebulizer 1. FIG. 41 shows the delivered state. FIG. 42 shows the activated state with the container 3 open.

In contrast to the other embodiments, in the twelfth embodiment, the nebulizer 1 is totally closed, and in particular, there is no need to push in, push on or otherwise mechanically (additionally) actuate an element, component or the like in order to activate or open the container 3. Instead, the activation of the nebulizer 1 or the opening of the container 3 occurs when the nebulizer 1 or pressure generator 5 is tensioned for the first time.

In the twelfth embodiment the container 3 and the conveying device for the fluid 2 in the nebulizer 1 are preferably matched to one another such that the conveying tube 9 or some other conveying element has not yet pierced the container 3 in the untensioned deliver state of the nebulizer 1. Only during the tensioning is the conveying tube 9 axially inserted into the container 3, thereby opening the container 3, and the holder 6 is brought into engagement with the container 3. The advantage for the user is that he does not have to take any special action in order to activate the device. Rather, the nebulizer 1 is automatically activated during normal use, i.e., when it is tensioned for the first time. The pre-installed container 3 thus results in a particularly simple and hence reliable means of operation for the user.

Preferably, in the twelfth embodiment, as in most of the other embodiments, the housing part 18 cannot be detached from the nebulizer 1. In particular, the housing part 18 is latched in position and is held so as to be non-removable, for example, in the pushed-on position by the latching arms 28 shown in the FIGS. 41 & 42.

Generally, it should be pointed out that, in the proposed nebulizer 1, the container 3 can preferably be inserted, i.e., incorporated in the nebulizer 1. Consequently, the container 3 is preferably a separate component. However, the container 3 may theoretically be formed directly by the nebulizer 1 or part of the nebulizer 1 or may otherwise be integrated in the nebulizer 1.

As already mentioned, individual features, aspects and/or principles of the embodiments described may also be combined with one another as desired and may be used particularly in the known nebulizer according to FIGS. 1 & 2 but also in similar or different nebulizers.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g., powder inhalers or so-called metered dose inhalers.

Preferably, the fluid 2 is a liquid, as already mentioned, especially an aqueous pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed hereinafter. As already stated, these may be aqueous or non-aqueous solutions, mixtures, formulations containing ethanol or free from solvent, or the like. It is particularly preferable for the fluid 2 to contain:

As pharmaceutically active substances, substance formulations or substance mixtures, all inhalable compounds are used such as, for example, inhalable macromolecules as disclosed in European Patent Application EP 1 003 478 and corresponding U.S. Patent Application Publication 2003/064032. Preferably, substances, substance formulations or substance mixtures for treating respiratory complaints and administered by inhalation are used.

Particularly preferred pharmaceutical compositions, in this context, are those which are selected from among the anticholinergic, betamimetics, steroids, phosphodiesterase IV inhibitors, LTD4 antagonists and EGFR kinase inhibitors, antiallergics, derivatives of ergot alkaloids, triptans, CGRP antagonists, phosphodiesterase V inhibitors, and combinations of such active substances, e.g. betamimetics plus anticholinergics or betamimetics plus antiallergics. In the case of combinations, preferably at least one of the active substances comprises chemically bound water. Preferably, anticholinergic-containing active substances are used, as monopreparations or in the form of combined preparations.

The following are specifically mentioned as examples of the active ingredients or the salts thereof:

Anticholinergics which may be used are preferably selected from among tiotropium bromide, oxitropium bromide, flutropium bromide, ipratropium bromide, glycopyrronium salts, trospium chloride, tolterodine, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenyl-propionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, cyclopropyltropine methyl 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide and scopine 9-hydroxymethyl-xanthene-9-carboxylate methobromide, optionally in the form of the racemates, enantiomers or diastereomers thereof and optionally in the form of the solvates and/or hydrates thereof.

Betamimetics which may be used are preferably selected from among albuterol, bambuterol, bitolterol, broxaterol, carbuterol, clenbuterol, fenoterol, formoterol, hexoprenaline, ibuterol, indacaterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzolsulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butyl amino]ethanol, 1-[2H-5-hydroxy-3-oxo-4H-1,4-benzoxazin-8-yl]-2-[3-(4-N,N-dimethylaminophenyl)-2-methyl-2-propyl amino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert.-butylamino)ethanol and 1-(4-ethoxycarbonylamino-3-cyano-5-fluorophenyl)-2-(tert.-butylamino)ethanol, optionally in the form of the racemates, enantiomers or diastereomers thereof and optionally in the form of the pharmacologically acceptable acid addition salts, solvates and/or hydrates thereof.

Steroids which may be used are preferably selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl 6α,9α-difluoro-17α-[(2-furanylcarbonyl)oxy]-11β-hydroxy-16α-methyl-3-oxo-androsta-1,4-diene-17β-carbothionate, (S)-(2-oxo-tetrahydro-furan-3S-yl) 6α,9α-difluoro-11β-hydroxy-16α-methyl-3-oxo-17α-propionyloxy-androsta-1,4-diene-17β-carbothionate and etiprednol-dichloroacetate (BNP-166), optionally in the form of the racemates, enantiomers or diastereomers thereof and optionally in the form of the salts and derivatives thereof, the solvates and/or hydrates thereof.

PDE IV-inhibitors which may be used are preferably selected from among enprofyllin, theophyllin, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropyl-methoxybenzamide, NCS-613, pumafentine, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl) cyclohexan-1-one, cis[4-cyano-4-(3-cyclopropylmethoxy-4-difluoromethoxyphenyl)cyclohexan-1-ol], (R)-(+)-ethyl [4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, CDP 840, Bay-198004, D-4418, PD-168787, T-440, T-2585, arofyllin, atizoram, V-11294A, C1-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridin, optionally in the form of the racemates, enantiomers or diastereomers thereof and optionally in the form of the pharmacologically acceptable acid addition salts, solvates and/or hydrates thereof.

LTD4-antagonists which may be used are preferably selected from among montelukast, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1 (R)-3 (3-(2-(2,3-dichlorothieno[3,2-b]pyridin-5-yl)-(E)-ethenyl)phenyl)-3-(2-(1-hydroxy-1-methylethyl)-phenyl) propyl)thio)methyl)cyclopropane-acetic acid, pranlukast, zafirlukast, [2-[[2-(4-tert-butyl-2-thiazolyl)-5-benzofuranyl] oxymethyl]phenyl]acetic acid, MCC-847 (ZD-3523), MN-001, MEN-91507 (LM-1507), VUF-5078, VUF-K-8707 and L-733321, optionally in the form of the racemates, enantiomers or diastereomers thereof, optionally in the form of the pharmacologically acceptable acid addition salts thereof and optionally in the form of the salts and derivatives thereof, the solvates and/or hydrates thereof.

EGFR-kinase inhibitors which may be used are preferably selected from among cetuximab, trastuzumab, ABX-EGF, Mab ICR-62, 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl) amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chlorofluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl) amino]-6-{[4-(N,N-dimethylamino)-1-oxo-2-buten-1-yl] amino}-7-[(R)-(tetra-hydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl) amino]-6-(4-hydroxy-phenyl)-7H-pyrrolo[2,3-d] pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl] amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl] amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl) carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl) amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl) carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylaminocyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts thereof, the solvates and/or hydrates thereof.

By acid addition salts, salts with pharmacologically acceptable acids which the compounds may possibly be capable of forming are meant, for example, salts selected from among the hydrochloride, hydrobromide, hydriodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of antiallergics are: disodium cromoglycate, nedocromil.

Examples of derivatives of the ergot alkaloids are: dihydroergotamine, ergotamine.

For inhalation, it is possible to use pharmaceutical compositions, pharmaceutical formulations and mixtures including the above-mentioned active substances, as well as the salts, esters and combinations of these active substances, salts and esters.

What is claimed is:

1. Nebulizer for a fluid comprising:
   a housing
   a container containing multiple doses of the fluid, said container being sealed off in a delivery state and disposed in the housing,
   a container opening device inside the housing which is adapted to open the container which is sealed off before or during a first use of the nebulizer, and
   a transportation lock for the container which, in the delivery state, is in engagement with the sealed container in a manner preventing the container from moving axially in the nebulizer in the delivery state and preventing opening of the container by the container opening device in the delivery state,
   wherein the transportation lock is releasable before or during a first use of the nebulizer,
   wherein the transportation lock comprises gripper arms for securing the container in the delivery state, and
   wherein the gripper arms are flexibly deflectable to open the transportation lock by axial movement of the container.

2. Nebulizer according to claim 1, wherein the container is movable in a stroke action, during at least one of conveying of the fluid, pressure generation and nebulization after disengagement of said transportation lock.

3. Nebulizer according to claim 1, wherein the gripper arms are distributed around the circumference of the container.

4. Nebulizer according to claim 1, wherein an inner part is provided for deflecting the gripper arms by axial engagement.

5. Nebulizer according to claim 1, wherein the gripper arms are secured in the delivery state against flexing or deflection.

6. Nebulizer according to claim 5, wherein a securing element is provided which secures the transportation lock against opening, the securing element being axially moveable to open the transportation lock.

7. Nebulizer according to claim 1, wherein the transportation lock is arranged completely inside the housing.

8. Nebulizer according to claim 1, wherein the gripper arms of the transportation lock engage on a base of the container or a transition of the container to the base of the container.

9. Nebulizer according to claim 1, wherein the transportation lock acts directly on the container.

10. Nebulizer according to claim 1, wherein the container is moveable in a stroke action relative to the housing after disengagement of said transportation lock.

11. Nebulizer according to claim 1, wherein the container is moveable in a stroke action inside the housing after disengagement of said transportation lock.

12. Nebulizer according to claim 1, wherein the housing comprises a housing part and wherein the transportation lock is releasable by axially pushing the housing part onto the nebulizer.

13. Nebulizer according to claim 1, wherein the housing comprises a housing part and wherein a removable securing member is provided for preventing, in the delivery state, axial pushing of the housing part so as to open the container.

14. Nebulizer according to claim 1, wherein the transportation lock comprises arms for holding the container in the delivery state, the arms being circumferentially arranged around the container.

15. Nebulizer according to claim 1, wherein the transportation lock circumferentially surrounds the container.

16. Nebulizer according to claim 1, wherein the transportation lock is releasable by completely closing the housing.

17. Nebulizer according to claim 1, wherein the transportation lock is released during opening the container.

18. Nebulizer according to claim 1, wherein the transportation lock is released after opening the container.

19. Nebulizer according to claim 1, wherein the housing is partially closed in the delivery state of the nebulizer.

20. Nebulizer according to claim 1, wherein the container opening device comprises means for opening the container by piercing.

* * * * *